United States Patent
Ben-Moshe et al.

(10) Patent No.: US 10,081,679 B2
(45) Date of Patent: Sep. 25, 2018

(54) COMPOSITIONS COMPRISING ANTI-CEACAM1 AND ANTI-PD ANTIBODIES FOR CANCER THERAPY

(71) Applicant: CCAM BIOTHERAPEUTICS LTD., Hod HaSharon (IL)

(72) Inventors: Tehila Ben-Moshe, Koranit (IL); Yair Sapir, Manof (IL); Ilana Mandel, Carmiel (IL); Edna Meilin, Kfar Veradim (IL)

(73) Assignee: CCAM BIOTHERAPEUTICS LTD., Hod Hasharon (IL)

( * ) Notice: Subject to any disclaimer, the term of this patent is extended or adjusted under 35 U.S.C. 154(b) by 0 days.

(21) Appl. No.: 15/039,022

(22) PCT Filed: Nov. 25, 2014

(86) PCT No.: PCT/IL2014/051019
§ 371 (c)(1),
(2) Date: May 24, 2016

(87) PCT Pub. No.: WO2015/075725
PCT Pub. Date: May 28, 2015

(65) Prior Publication Data
US 2017/0166637 A1 Jun. 15, 2017

Related U.S. Application Data

(60) Provisional application No. 61/908,190, filed on Nov. 25, 2013.

(51) Int. Cl.
| | | |
|---|---|---|
| A61K 39/395 | (2006.01) | |
| C07K 16/28 | (2006.01) | |
| A61K 35/17 | (2015.01) | |
| A61K 39/00 | (2006.01) | |
| A61K 35/12 | (2015.01) | |

(52) U.S. Cl.
CPC .......... *C07K 16/2803* (2013.01); *A61K 35/17* (2013.01); *A61K 39/39558* (2013.01); *C07K 16/2827* (2013.01); A61K 2035/124 (2013.01); A61K 2039/507 (2013.01); C07K 2317/33 (2013.01); C07K 2317/565 (2013.01); C07K 2317/92 (2013.01)

(58) Field of Classification Search
None
See application file for complete search history.

(56) References Cited

U.S. PATENT DOCUMENTS

| 4,816,567 A | 3/1989 | Cabilly et al. |
|---|---|---|
| 4,946,778 A | 8/1990 | Ladner et al. |
| 5,091,513 A | 2/1992 | Huston et al. |
| 5,096,815 A | 3/1992 | Ladner et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,750,373 A | 5/1998 | Garrard et al. |
| 2015/0273056 A1* | 10/2015 | Blumberg .......... A61K 31/7088 424/136.1 |

FOREIGN PATENT DOCUMENTS

| EP | 0404097 A2 | 12/1990 |
|---|---|---|
| WO | 93/11161 A1 | 6/1993 |
| WO | 93/15210 A1 | 8/1993 |
| WO | 96/13583 A2 | 5/1996 |
| WO | 96/37621 A2 | 11/1996 |
| WO | 99/52552 A1 | 10/1999 |
| WO | 2010/027827 A2 | 3/2010 |
| WO | 2010/036959 A2 | 4/2010 |
| WO | 2010/125571 A1 | 11/2010 |
| WO | 2011/066342 A2 | 6/2011 |
| WO | 2013/054331 A1 | 4/2013 |
| WO | 2014/022332 A1 | 2/2014 |
| WO | 2014/059251 A1 | 4/2014 |

OTHER PUBLICATIONS

Bird et al., (1988) Single-chain antigen-binding proteins. Science 242(4877): 423-6.
Blank et al., (2005) Interaction of PD-L1 on tumor cells with PD-1 on tumor-specific T cells as a mechanism of immune evasion: implications for tumor immunotherapy. Cancer Immunol Immunother 54(4): 307-14.
Boerner et al., (1991) Production of antigen-specific human monoclonal antibodies from in vitro-primed human splenocytes. J Immunol 147(1): 86-95.
Chemnitz et al., (2004) SHP-1 and SHP-2 associate with immunoreceptor tyrosine-based switch motif of programmed death 1 upon primary human T cell stimulation, but only receptor ligation prevents T cell activation. J Immunol 173(2): 945-54.
Clackson et al., (1991) Making antibody fragments using phage display libraries. Nature 352(6336): 624-8.
Curran et al., (2010) PD-1 and CTLA-4 combination blockade expands infiltrating T cells and reduces regulatory T and myeloid cells within B16 melanoma tumors. Proc Natl Acad Sci U S A 107(9): 4275-80.
Ettinghausen et al., (1985) Recombinant interleukin 2 stimulates in vivo proliferation of adoptively transferred lymphokine-activated killer (LAK) cells. J Immunol 135(5): 3623-35.
Ettinghausen et al., (1985) Systemic administration of recombinant interleukin 2 stimulates in vivo lymphoid cell proliferation in tissues. J Immunol 135(2): 1488-97.

(Continued)

*Primary Examiner* — Laura B Goddard
*Assistant Examiner* — Meera Natarajan
(74) *Attorney, Agent, or Firm* — Rothwell Figg Ernst & Manbeck P.C.

(57) ABSTRACT

The present invention provides compositions comprising anti-CEACAM1 antibodies, compositions comprising antibodies capable of inhibiting or blocking the interaction between PD-1 and its ligands, and methods for their combined use in treating cancer.

18 Claims, 9 Drawing Sheets

Specification includes a Sequence Listing.

(56) References Cited

OTHER PUBLICATIONS

Fiori et al., (2012) The expression and modulation of CEACAM1 and tumor cell transformation. Ann 1st Super Sanita 48(2): 161-71.
Fishwild et al., (1996) High-avidity human IgG kappa monoclonal antibodies from a novel strain of minilocus transgenic mice. Nat Biotechnol 14(7): 845-51.
Gray-Owen and Blumberg (2006) CEACAM1: contact-dependent control of immunity. Nat Rev Immunol 6(6): 433-46.
Holliger et al., (1993) "Diabodies": small bivalent and bispecific antibody fragments. Proc Natl Acad Sci U S A 90(14): 6444-8.
Hoogenboom and Winter (1992) By-passing immunisation. Human antibodies from synthetic repertoires of germline VH gene segments rearranged in vitro. J Mol Biol 227(2): 381-8.
Houot and Levy (2009) T-cell modulation combined with intratumoral CpG cures lymphoma in a mouse model without the need for chemotherapy. Blood 113(15): 3546-52.
Huang et al., (2015) CEACAM1 regulates T1M-3-mediated tolerance and exhaustion. Nature 517(7534): 386-90.
Huston et al., (1988) Protein engineering of antibody binding sites: recovery of specific activity in an anti-digoxin single-chain Fv analogue produced in *Escherichia coli*. Proc Natl Acad Sci U S A 85(16): 5879-83.
Introna et al., (2013) Cytokine Induced Killer (CIK) cells for the treatment of haematological neoplasms. Immunol Lett 155(1-2): 27-30.
Jones et al., (1986) Replacing the complementarity-determining regions in a human antibody with those from a mouse. Nature 321(6069): 522-5.
Köhler and Milstein (1975) Continuous cultures of fused cells secreting antibody of predefined specificity. Nature 256 (5517): 495-7.
Lefranc et al., (1999) IMGT, the international ImMunoGeneTics database. Nucleic Acids Res 27(1): 209-12.
Lonberg and Huszar (1995) Human antibodies from transgenic mice. Int Rev Immunol 13(1): 65-93.
Lonberg et al., (1994) Antigen-specific human antibodies from mice comprising four distinct genetic modifications. Nature 368(6474): 856-9.
Lu et al., (2014) Clinical evaluation of compounds targeting PD-1/PD-L1 pathway for cancer immunotherapy. J Oncol Pharm Pract, 17 pages.
Mangsbo et al., (2010) Enhanced tumor eradication by combining CTLA-4 or PD-1 blockade with CpG therapy. J Immunother 33(3): 225-35.
Marks et al., (1991) By-passing immunization. Human antibodies from V-gene libraries displayed on phage. J Mol Biol 222(3): 581-97.
Marks et al., (1992) By-passing immunization: building high affinity human antibodies by chain shuffling. Biotechnology (N Y) 10(7): 779-83.
Morales et al., (1999) Regulation of human intestinal intraepithelial lymphocyte cytolytic function by biliary glycoprotein (CD66a). J Immunol 163(3): 1363-70.
Morrison (1994) Immunology. Success in specification. Nature 368(6474): 812-3.
Müller et al., (1998) A dimeric bispecific miniantibody combines two specificities with avidity. FEBS Lett 432(1-2): 45-9.

Neuberger (1996) Generating high-avidity human Mabs in mice. Nat Biotechnot 14(7): 826.
Okazaki and Honjo (2007) PD-1 and PD-1 ligands: from discovery to clinical application. Int Immunol 19(7): 813-24.
Ortenberg et al., (2012) Novel immunotherapy for malignant melanoma with a monoclonal antibody that blocks CEACAM1 homophilic interactions. Mol Cancer Ther 11(6): 1300-10.
Phillips et al., (1987) In vivo and in vitro activation of natural killer cells in advanced cancer patients undergoing combined recombinant interleukin-2 and LAK cell therapy. J Clin Oncol. Dec. 1987;5(12): 1933-41.
Presta (1992) Antibody Engineering. Curr Opin Struct Biol 2(4):593-596.
Riechmann et al., (1988) Reshaping human antibodies for therapy. Nature 332(6162):323-329.
Sapoznik et al., (2012) Novel Anti-Melanoma Immunotherapies: Disarming Tumor Escape Mechanisms. Clinical and Developmental Immunology 2012 (2012), Article ID 818214; 9 pages.
Sheets et al., (1998) Efficient construction of a large nonimmune phage antibody library: the production of high-affinity human single-chain antibodies to protein antigens. Proc Natl Acad Sci U S A 95(11): 6157-62.
Taylor et al., (1992) A transgenic mouse that expresses a diversity of human sequence heavy and light chain immunoglobulins. Nucleic Acids Res 20(23): 6287-95.
Topalian et al., (2012) Targeting the PD-1/B7-H1(PD-L1) pathway to activate anti-tumor immunity. Curr Opin Immunol 24(2): 207-12.
Vaughan et al., (1996) Human antibodies with sub-nanomolar affinities isolated from a large non-immunized phage display library. Nat Biotechnol 14(3): 309-14.
Ward et al., (1989) Binding activities of a repertoire of single immunoglobulin variable domains secreted from *Escherichia coli*. Nature 341(6242): 544-6.
Watt et al., (2001) Homophilic adhesion of human CEACAM1 involves N-terminal domain interactions: structural analysis of the binding site. Blood 98(5): 1469-79.
Wu and Kabat (1970) An analysis of the sequences of the variable regions of Bence Jones proteins and myeloma light chains and their implications for antibody complementarity. J Exp Med 132(2): 211-50.
Zapata et al., (1995) Engineering linear F(ab')2 fragments for efficient production in *Escherichia coil* and enhanced antiproliferative activity. Protein Eng 8(10): 1057-62.
KEYTRUDA®, highlights of prescribing information. Retrieved from https://www.merck.com/product/usa/pi_circulars/k/keytruda/keytruda_pi.pdf; revised Dec. 2015 (Dec. 2015). 22 pages.
Markel et al., (2016) Inhibition of the novel immune checkpoint CEACAM1 to enhance anti-tumor immunological activity. J Clin Oncol 34 (suppl; abstr 3044). Retrieved from the Internet: URL: http://meetinglibrary.asco.org/print/2390256; 2 pages.
Tehila Ben MosheBen Moshe (2016) CM-24 / MK-6018, a novel anti CEACAM1 therapy for treating cancer. ICI Meeting, Boston, Mar. 2016. 36 pages.
Carroll (2017); Endpoints News 24.3.2017; That $95M Merck gamble to acquire cCAM? It didn't pay off. Retrieved on Mar. 1, 2018 from URL: https://endpts.com/that-95m-merck-gamble-to-acquire-ccam-it-didnt-pay-off/. 2 pages.

\* cited by examiner

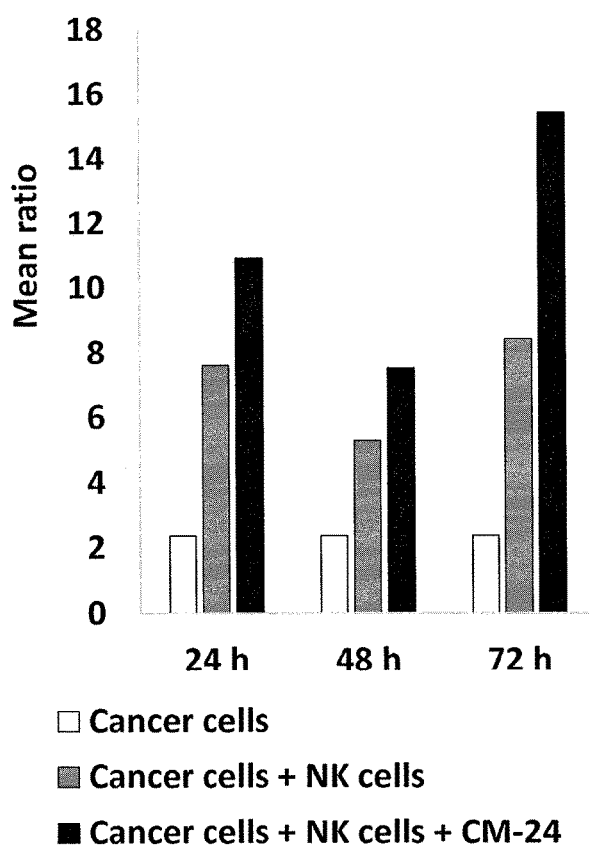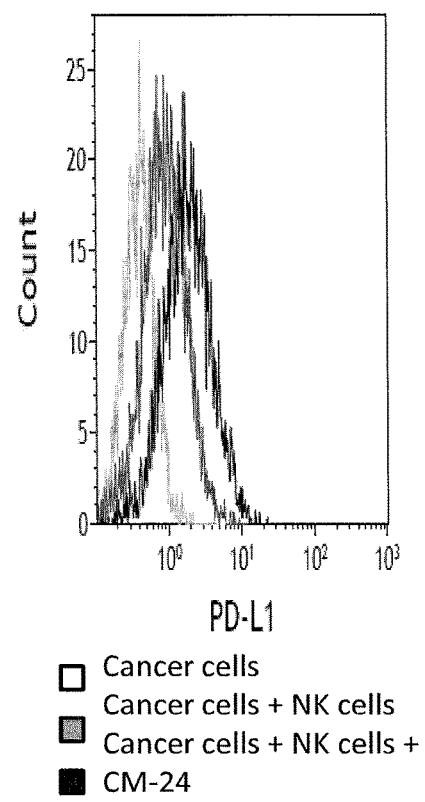
FIGURE 7A
FIGURE 7B

COMPOSITIONS COMPRISING ANTI-CEACAM1 AND ANTI-PD ANTIBODIES FOR CANCER THERAPY

CROSS-REFERENCE TO RELATED APPLICATIONS

The present application is a national stage filing under 35 U.S.C. § 371 of PCT/IL2014/051019, filed on 25 Nov. 2014, and claims the benefit of priority to U.S. Provisional Application No. 61/908,190, filed 25 Nov. 2013. Each application is incorporated herein by reference in its entirety.

FIELD OF THE INVENTION

The present invention relates to cancer immunotherapy, in particular to combinations of anti-CEACAM1 and anti-PD-1/PD-Ligand antibodies, and their use in treating cancer.

BACKGROUND OF THE INVENTION

The transmembrane protein carcinoembryonic antigen-related cell adhesion molecule 1 (CEACAM1, also known as biliary glycoprotein (BGP), CD66a and C-CAM1), is a member of the carcinoembryonic antigen family (CEA) that also belongs to the immunoglobulin superfamily. Human CEACAM1 has been assigned the SwissProt accession number P13688. CEACAM1 interacts with itself and with other known CEACAM proteins, including CD66e (CEACAM6) and CD66e (CEACAM5, CEA) proteins. It is expressed on a wide spectrum of cells, ranging from epithelial cells to those of hemopoietic origin (e.g. immune cells).

Many different functions have been attributed to the CEACAM1 protein. It was shown that the CEACAM1 protein is over expressed in some carcinomas of colon, prostate, as well as other types of cancer, such as melanoma. Additional data support the central involvement of CEACAM1 in angiogenesis and metastasis. CEACAM1 also plays a role in the modulation of innate and adaptive immune responses. For example, CEACAM1 was shown to be an inhibitory receptor for activated T cells contained within the human intestinal epithelium (WO 99/52552 and Morales et al. J. Immunol. 1999, 163, 1363-1370). Additional reports have indicated that CEACAM1 engagement either by T cell receptor cross-linking with monoclonal antibodies (mAbs) or by *Neisseria* gonorrhea Opa proteins inhibits T cell activation and proliferation. Several monoclonal antibodies against the CEACAM1 protein are already known, such as 26H7, 5F4, TEC-11, 12-140-4, 4/3/17, COL-4, F36-54, 34B1, YG-C28F2, D14HD11, b18.7.7, D11-ADM HEA81, B1.1, CLB-gran-10, F34-187, T84.1, B6.2, B1.13, YG-C94G7, 12-140-5, TET-2 and scFv-DIATHIS1 (Watt et al., Blood, 2001, Vol. 98, pages 1469-1479). WO 2010/12557 describes the murine a monoclonal antibody to human CEACAM1. WO 2013/054331 describes the chimeric a monoclonal antibody to human CEACAM1 CM10.

Programmed cell death protein 1 (PD-1) is a type I transmembrane protein belonging to the CD28/CTLA-4 family of immuno-receptors that mediate signals for regulating immune responses. Human PD-1 has been assigned the SwissProt accession number Q15116. Members of the CD28/CTLA-4 family either up-regulate (CD28 and ICOS) or down-regulate T cell activation (CTLA-4 and PD-1). PD-1 is expressed on activated T cells, B cells, myeloid cells and on a subset of thymocytes. Several monoclonal antibodies against the PD-1 protein are already known, such as MK-3475 (humanized IgG4 mAb), AMP514, BMS-936558 (fully human IgG4 mAb), and pidilizumab also known as CT-011 (humanized IgG1 mAb) (Topalian et al., Curr. Opin. Immunol., 2012, Vol. 24(2), pages 207-212).

Programmed cell death-ligand 1 (PD-L1) also known as cluster of differentiation 274 (CD274) or B7 homolog 1 (B7-H1) is a protein that in humans is encoded by the CD274 gene. PD-L1 is a 40 kDa type 1 transmembrane protein that has been speculated to play a major role in suppressing the immune system during particular events such as pregnancy, tissue allografts, and other disease states such as hepatitis. Normally, the immune system reacts to foreign antigens where there is some accumulation in the lymph nodes or spleen which triggers a proliferation of antigen-specific $CD8^+$ T cell. The formation of PD-1/PD-L1 ligand complex transmits an inhibitory signal which reduces the proliferation of these $CD8^+$ T cells at the lymph nodes and supplementary to that PD-1 is also able to control the accumulation of foreign antigen specific T cells in the lymph nodes through apoptosis which is further mediated by a lower regulation of the gene Bcl-2 (Chemnitz J M et al., 2004, Journal of Immunology, 173(2): 945-54). Engagement of PD-L1 with its receptor PD-1 found on activated T cells, B cells, and myeloid cells delivers a signal that inhibits TCR-mediated activation of IL-2 production and T cell proliferation. Programmed cell death 1 ligand 2 (also known as PD-L2, B7-DC) is a protein that in humans is encoded by the PDCD1LG2 gene. PDCD1LG2 has also been designated as CD273 (cluster of differentiation 273).

PD-1 and its ligands, PD-L1 and PD-L2, deliver inhibitory signals that regulate the balance between T cell activation, tolerance, and immunopathology Immune responses to foreign and self-antigens require specific and balanced responses to clear pathogens and tumors and yet maintain tolerance. Human PD-L1 and PD-L2 have been assigned the SwissProt accession numbers Q9NZQ7 and Q9BQ51, respectively. Induction and maintenance of T cell tolerance requires PD-1, and its ligand PD-L1 on nonhematopoietic cells can limit effector T cell responses and protect tissues from immune-mediated tissue damage. The PD-1:PD-L pathway also has been usurped by microorganisms and tumors to attenuate antimicrobial or tumor immunity and facilitate chronic infection and tumor survival. Several monoclonal antibodies against the PD-L1 protein are already known, such as MEDI-4736, BMS-936559, MSB0010718C and MPDL3280A (Lu et al., J. Oncol. Pharm. Pract., 2014). Other monoclonal antibodies against the PD-L2 protein are also known, such as those disclosed in PCT application publication nos. WO/2010/027827, WO/2010/036959 and WO/2011/066342. WO/2014/059251 relates to compositions and methods for enhancing the immune response and/or reducing T cell tolerance in subjects by administering inhibitors of two or more of CEACAM1, PD-1 and/or latency associated peptide (LAP).

Cancer immunotherapy is the use of the immune system to treat cancer. There are three main groups of immunotherapy: cell-based therapies, antibody therapies and cytokine therapies. They all exploit the fact that cancer cells often have different molecules on their surface that can be detected by the immune system. These molecules are known as cancer antigens. Immunotherapy is used to provoke the immune system into attacking the tumor cells by using these cancer antigens as targets.

Antibody therapies are currently the most successful form of immunotherapy, with many approved treatments for a wide range of cancers. Antibodies are proteins produced by the immune system that bind to a target antigen on the surface of a cell. In normal physiology they are used by the immune system to fight pathogens. Each antibody is specific to one or few highly similar proteins and those that bind to cancer antigens are used in the treatment of cancer. Once bound to a cancer antigen, antibodies can induce antibody-dependent cell-mediated cytotoxicity, activate the complement system, prevent a receptor interacting with its ligand or deliver a payload of chemotherapy or radiation, all of which can lead to cell death. There are antibodies currently approved for the treatment of cancer by the U.S. Food and drug administration (FDA): Rituximab (1997), Trastuzumab (1998), Gemtuzumab ozogamicin (2000), Alemtuzumab (2001), Ibritumomab tiuxetan (2002), Tositumomab (2003), Cetuximab (2004), Bevacizumab (2004), Panitumumab (2006), Ofatumumab (2009), Ipilimumab (2011) and Brentuximab vedotin (2011).

While originally approved as anti-cancer monotherapies, several antibodies were further approved for use in combination with other anti-cancer therapies, such as chemotherapy. For example, the FDA granted approval to Rituximab (Rituxan, Genentech, Inc.) in combination with fludarabine and cyclophosphamide for the treatment of both previously untreated and previously treated patients with chronic lymphocytic leukemia (CLL). Recently, the FDA approved Bevacizumab (Avastin, Genentech, Inc.) in combination with paclitaxel and either cisplatin or topotecan for the treatment of persistent, recurrent, or metastatic cervical cancer.

There remains an unmet need for improved combinatorial antibody-based therapies, employing a diversity of antibodies targeting distinct or parallel mechanisms of cancer progression.

SUMMARY OF THE INVENTION

The present invention provides improved combinatorial antibody-based therapies, employing a plurality of antibodies targeting distinct or parallel mechanisms of cancer progression. The present invention stems from the surprising finding that combinations of anti-CEACAM1 antibodies and antibodies directed to disrupt the binding of PD-1 to its natural ligands, PD-L1 and PD-L2, significantly and synergistically elevated the cytotoxicity of lymphocyte cells, such as tumor-infiltrating-lymphocyte (TIL) cells and lymphokine-activated killer (LAK) cells, toward different types of cancer. It is now disclosed for the first time that step-wise pre-incubation of the lymphocyte cells with these two types of antibodies, rather than concurrent incubation, maximizes the lymphocyte mediated cytotoxicity. This unexpected finding advantageously can be exploited for improved clinical outcome, where different antibodies are separately administered to cancer patients to maximize efficacy. Another surprising finding was that blocking of CEACAM1 by anti-CEACAM1 antibodies increases PD-L1 expression on cancer cells. Furthermore, for the first time it was found that antibody combinations of anti-CEACAM1 antibodies and antibodies directed to disrupt the binding of PD-1 to its natural ligands, PD-L1 and PD-L2, synergistically attenuated the progression of established tumors in an immunocompetent murine model.

The present invention thus provides, in one aspect, a pharmaceutical composition comprising a monoclonal antibody to human carcinoembryonic antigen-related cell adhesion molecule 1 (CEACAM1) or an antigen-binding fragment thereof, and a pharmaceutical composition comprising a monoclonal antibody to at least one of human programmed cell death protein 1 (PD-1), PD-L1 and PD-L2 or an antigen-binding fragment thereof, for use in treatment of cancer by separate administration.

The present invention further provides, in another aspect, a pharmaceutical composition comprising a monoclonal antibody to human-carcinoembryonic antigen-related cell adhesion molecule 1 (CEACAM1) or an antigen-binding fragment thereof, and a pharmaceutical composition comprising a monoclonal antibody capable of inhibiting or blocking the interaction between human programmed cell death protein 1 (PD-1) and its ligands or an antigen-binding fragment thereof, for use in treatment of cancer by separate administration.

The present invention further provides, in another aspect, a monoclonal antibody to human-carcinoembryonic antigen-related cell adhesion molecule 1 (CEACAM1) or an antigen-binding fragment thereof, and a monoclonal antibody capable of inhibiting or blocking the interaction between human programmed cell death protein 1 (PD-1) and its ligands or an antigen-binding fragment thereof, for use in treatment of cancer by separate administration.

The present invention further provides, in yet another aspect, a method for treating a patient having cancer, comprising administering to the patient a pharmaceutical composition comprising a monoclonal antibody to human CEACAM1 or an antigen-binding fragment thereof, and a pharmaceutical composition comprising a monoclonal antibody to at least one of human PD-1, PD-L1 and PD-L2 or an antigen-binding fragment thereof, thereby treating the cancer.

The present invention provides, in another aspect, a kit comprising a pharmaceutical composition comprising a monoclonal antibody to human CEACAM1 or an antigen-binding fragment thereof, and a pharmaceutical composition comprising a monoclonal antibody to at least one of human PD-1, PD-L1 and PD-L2 or an antigen-binding fragment thereof.

The present invention provides, in another aspect, the kit described above, for use in treating cancer.

In some embodiments, the monoclonal antibody to human CEACAM1 or an antigen-binding fragment thereof is capable of binding with an affinity of at least about $10^{-8}$M to a human CEACAM1 protein. Each possibility represents a separate embodiment of the invention. In some embodiments, the monoclonal antibody to human CEACAM1 or an antigen-binding fragment thereof is capable of binding with an affinity of at least about $5\times10^{-7}$M to at least one of a human CEACAM3 and human CEACAM5 protein. Each possibility represents a separate embodiment of the invention.

In some embodiments, the monoclonal antibody to human CEACAM1 is selected from the group consisting of CM-24, 26H7, 5F4, TEC-11, 12-140-4, 4/3/17, COL-4, F36-54, 34B1, YG-C28F2, D14HD11, b18.7.7, D11-ADM HEA81, B1.1, CLB-gran-10, F34-187, T84.1, B6.2, B1.13, YG-C94G7, 12-140-5, scFv DIATHIS1, TET-2, antigen-binding fragments thereof, and any combination thereof. Each possibility represents a separate embodiment of the invention. In a particular embodiment, the monoclonal antibody to human CEACAM1 is CM-24 or an antigen-binding fragment thereof, or any combination thereof. Each possibility represents a separate embodiment of the invention.

In some embodiments, the monoclonal antibody or fragment thereof which recognizes CEACAM1, comprises at least one heavy-chain CDR comprising a sequence selected from the group consisting of: SEQ ID NO: 1, SEQ ID NO: 2 and SEQ ID NO: 3, and at least one light-chain CDR comprising a sequence selected from the group consisting of: SEQ ID NO: 4, SEQ ID NO: 5 and SEQ ID NO: 6. Each possibility represents a separate embodiment of the invention. In some embodiments, the monoclonal antibody or fragment thereof which recognizes CEACAM1, comprises at least two heavy-chain CDRs comprising a sequence selected from the group consisting of: SEQ ID NO: 1, SEQ ID NO: 2 and SEQ ID NO: 3, and at least one light-chain CDRs comprising a sequence selected from the group consisting of: SEQ ID NO: 4, SEQ ID NO: 5 and SEQ ID NO: 6. Each possibility represents a separate embodiment of the invention.

In some embodiments, the monoclonal antibody or fragment thereof which recognizes CEACAM1, comprises at least one heavy-chain CDR sequence of at least five consecutive amino acids derived from a sequence selected from the group consisting of: SEQ ID NO: 19, SEQ ID NO: 20 and SEQ ID NO: 21, and at least one light-chain CDR sequence of at least five amino acids derived from a sequence selected from the group consisting of: SEQ ID NO: 22, SEQ ID NO: 23 and SEQ ID NO: 24. Each possibility represents a separate embodiment of the invention.

In some embodiments, the binding site of the monoclonal antibody or fragment thereof which recognizes CEACAM1 consists of the six CDRs of SEQ ID NOs: 1, 2, 3, 4, 5, and 6. In some embodiments, the binding site of the monoclonal antibody or fragment thereof which recognizes CEACAM1 consists of the six CDRs of SEQ ID NOs: 7, 8, 9, 10, 11, and 12. In some embodiments, the binding site of the monoclonal antibody or fragment thereof which recognizes CEACAM1 consists of the six CDRs of SEQ ID NOs: 13, 14, 15, 16, 17, and 18. In some embodiments, the binding site of the monoclonal antibody or fragment thereof which recognizes CEACAM1 consists of the six CDRs of SEQ ID NOs: 19, 20, 21, 22, 23, and 24.

In certain embodiments, the monoclonal antibody or an antigen-binding fragment thereof which recognizes human CEACAM1 comprises a heavy-chain CDR1 comprising a sequence set forth in SEQ ID NO: 1, a heavy-chain CDR2 comprising a sequence set forth in SEQ ID NO: 2, a heavy-chain CDR3 comprising a sequence set forth in SEQ ID NO: 3, a light-chain CDR1 comprising a sequence set forth in SEQ ID NO: 4, a light-chain CDR2 comprising a sequence set forth in SEQ ID NO: 5 and a light-chain CDR3 comprising a sequence set forth in SEQ ID NO: 6, and analogs and derivatives thereof.

In certain embodiments, the monoclonal antibody or an antigen-binding fragment thereof which recognizes human CEACAM1 comprises a heavy chain CDR1 having the sequence set forth in SEQ ID NO: 7, heavy chain CDR2 having the sequence set forth in SEQ ID NO: 8 and heavy chain CDR3 having the sequence set forth in SEQ ID NO: 9. In certain embodiments, the monoclonal antibody or antigen-binding fragment thereof which recognizes human CEACAM1 comprises a heavy chain CDR1 having the sequence set forth in SEQ ID NO: 13, heavy chain CDR2 having the sequence set forth in SEQ ID NO: 14 and heavy chain CDR3 having the sequence set forth in SEQ ID NO: 15.

In certain embodiments, the monoclonal antibody or antigen-binding fragment thereof which recognizes human CEACAM1 comprises a light chain CDR1 having the sequence set forth in SEQ ID NO: 10, light chain CDR2 having the sequence set forth in SEQ ID NO: 11 and light chain CDR3 having the sequence set forth in SEQ ID NO: 12. In certain embodiments, the monoclonal antibody or an antigen-binding fragment thereof which recognizes human CEACAM1 comprises a light chain CDR1 having the sequence set forth in SEQ ID NO: 16, light chain CDR2 having the sequence set forth in SEQ ID NO: 17, and light chain CDR3 having the sequence set forth in SEQ ID NO: 18.

In certain embodiments, the monoclonal antibody or an antigen-binding fragment thereof which recognizes human CEACAM1 comprises CDR sequences set forth in SEQ ID NOs: 13, 14, 15, 16, 17, and 18. In certain embodiments, the monoclonal antibody or an antigen-binding fragment thereof which recognizes human CEACAM1 comprises CDR sequences set forth in SEQ ID NOs: 7, 8, 9, 10, 11, and 12.

In certain embodiments, the monoclonal antibody or an antigen-binding fragment thereof which recognizes human CEACAM1 comprises a heavy chain variable domain sequence having a sequence set forth in SEQ ID NO: 25, or an analog or derivative thereof having at least 97% sequence identity with said heavy chain sequence. In certain embodiments, the monoclonal antibody or an antigen-binding fragment thereof which recognizes human CEACAM1 comprises a light chain variable domain sequence having a sequence set forth in SEQ ID NO: 26, or an analog or derivative thereof having at least 97% sequence identity with said light chain sequence. In certain embodiments, the monoclonal antibody or an antigen-binding fragment thereof which recognizes human CEACAM1 comprises a heavy chain variable domain having a sequence set forth in SEQ ID NO: 25 and a light chain variable domain having a sequence set forth in SEQ ID NO: 26, or an analog or derivative thereof having at least 97% sequence identity with the antibody or fragment sequence.

In certain embodiments, the monoclonal antibody or an antigen-binding fragment thereof which recognizes human CEACAM1 comprises:
  i. a framework sequence selected from the group consisting of: mouse IgG2a, mouse IgG2b, mouse IgG3, human IgG1, human IgG2, human IgG3; and
  ii. six CDRs having sequences set forth in SEQ ID NOs: 13, 14, 15, 16, 17, and 18; or six CDRs having sequences set forth in SEQ ID NOs: 7, 8, 9, 10, 11, and 12; and
analogs and derivatives thereof having at least 97% sequence identity with said CDR sequences, wherein the monoclonal antibody or fragment binds with an affinity of at least about $5 \times 10^{-7}$ M to at least two CEACAM subtypes.

In certain embodiments, the monoclonal antibody or an antigen-binding fragment thereof which recognizes human CEACAM1 comprises human derived constant regions selected from the group consisting of: human IgG1, human IgG2, and human IgG3. In certain embodiments, the human or humanized monoclonal antibody or an antigen-binding fragment thereof which recognizes human CEACAM1 comprises a constant region subclass of human IgG1 subtype.

In certain embodiments, the human or humanized monoclonal antibody or an antigen-binding fragment thereof which recognizes human CEACAM1 comprises the six CDRs having sequences set forth in SEQ ID NOs: 13, 14, 15, 16, 17, and 18; or the six CDRs having sequences set forth in SEQ ID NOs: 7, 8, 9, 10, 11, and 12; and analogs and derivatives thereof having at least 95% sequence identity with said CDR sequences, wherein the monoclonal antibody binds with an affinity of at least about $10^{-8}$ M to CEACAM1.

In certain embodiments, the human or humanized monoclonal antibody or an antigen-binding fragment thereof which recognizes human CEACAM1 comprises a heavy chain sequence set forth in SEQ ID NO: 27. In certain embodiments, the human or humanized monoclonal antibody or an antigen-binding fragment thereof which recognizes human CEACAM1 comprises a light chain sequence set forth in SEQ ID NO: 28. In certain embodiments, the human or humanized monoclonal antibody or an antigen-binding fragment thereof which recognizes human CEACAM1 comprises a heavy chain sequence set forth in SEQ ID NO: 27, and light chain sequence set forth in SEQ ID NO: 28.

In certain embodiments, the monoclonal antibody or an antigen-binding fragment thereof which recognizes human CEACAM1 comprises at least the antigen-binding portion, which is capable of binding the same epitope on the CEACAM1 molecule to which a monoclonal antibody having the six CDR sequences set forth in SEQ ID NOs: 7, 8, 9, 10, 11 and 12, or the six CDR sequences set forth in SEQ ID NOs: 13, 14, 15, 16, 17 and 18, binds. In certain embodiments, the monoclonal antibody or an antigen-binding fragment thereof is reactive with an epitope within residues 17-29 and 68-79 of human CEACAM1 having the sequences VLLLVHNLPQQLF (SEQ ID NO:32) and YPNASLLIQNVT (SEQ ID NO:33) respectively.

In certain embodiments, the monoclonal antibody or an antigen-binding fragment thereof is reactive with an epitope comprising at least four amino acids of the sequence VLLL-VHNLPQQLF (SEQ ID NO: 29). In certain embodiments, the monoclonal antibody or an antigen-binding fragment thereof is reactive with an epitope comprising amino acid residues within the sequences VLLLVHNLPQQLF (SEQ ID NO: 29) and YPNASLLIQNVT (SEQ ID NO: 30). In certain embodiments, the monoclonal antibody or an antigen-binding fragment thereof is reactive with an epitope within sequences VLLLVHNLPQQLF (SEQ ID NO: 29) and PNASLLI (SEQ ID NO: 31).

In certain embodiments, the antigen-binding fragment retains at least 10%, at least 20%, at least 30%, at least 40%, at least 50%, at least 60%, at least 70%, at least 80% or at least 90% of the corresponding full length antibody's affinity to the indicated epitope or antigen. Each possibility represents a separate embodiment of the invention. In certain embodiments, the antigen-binding fragment retains at least 50% of the corresponding full length antibody's affinity to the indicated epitope or antigen. In certain embodiments, the antigen-binding fragment retains at least 90% of the corresponding full length antibody's affinity to the indicated epitope or antigen.

In some embodiments, the monoclonal antibody to human PD-1 is selected from the group consisting of MK-3475, AMP514, BMS-936558, CT-011, antigen-binding fragments thereof, and any combination thereof. Each possibility represents a separate embodiment of the invention. In some embodiments, the monoclonal antibody to human PD-L1 is selected from the group consisting of MEDI-4736, BMS-936559, MSB0010718C, MPDL3280A, antigen-binding fragments thereof, and any combination thereof. Each possibility represents a separate embodiment of the invention. In some embodiments, thenti-PD-L1 antibody is AMP-224.

In some embodiments, the monoclonal antibody to human CEACAM1 is a human or humanized monoclonal antibody. Each possibility represents a separate embodiment of the invention. In some embodiments, the monoclonal antibody to human PD-1 is a human or humanized monoclonal antibody. Each possibility represents a separate embodiment of the invention. In some embodiments, the monoclonal antibody to human PD-L1 is a human or humanized monoclonal antibody. Each possibility represents a separate embodiment of the invention. In some embodiments, the monoclonal antibody to human PD-L2 is a human or humanized monoclonal antibody. Each possibility represents a separate embodiment of the invention. In certain embodiments, a human antibody is an isolated human antibody, i.e. isolated from a human donor. In certain embodiments, a human antibody is a human antibody isolated from a hybridoma cell line. In certain embodiments, a human antibody refers to a recombinant human antibody, i.e. produced by recombinant DNA technology.

In certain embodiments, the pharmaceutical compositions described above further comprise a lymphocyte cell or a plurality of lymphocyte cells.

In some embodiments, the lymphocyte cell expresses CEACAM1, PD-1, or both. Each possibility represents a separate embodiment of the present invention. In certain such embodiments, the lymphocyte cell expresses CEACAM1 and PD-1.

In some embodiments, the lymphocyte cell is selected from the group consisting of a tumor-infiltrating-lymphocyte (TIL) cell, a lymphokine-activated killer (LAK) cell, a cytokine induced killer (CIK) cell, a T cell, a B cell, an NK cell, and any combination thereof. Each possibility represents a separate embodiment of the present invention. In certain such embodiments, the lymphocyte cell is selected from the group consisting of a tumor-infiltrating-lymphocyte (TIL) cell and a lymphokine-activated killer (LAK) cell. In certain such embodiments, the lymphocyte cell is a tumor-infiltrating-lymphocyte (TIL) cell or a plurality of TIL cells. In certain such embodiments, the lymphocyte cell is a lymphokine-activated killer (LAK) cell or a plurality of LAK cells.

In certain embodiments, the lymphocyte cell is activated. In some embodiments, the lymphocyte cell is cytotoxic to a cancer cell.

In some embodiments, the cancer cell expresses CEACAM1, PD-L1, PD-L2, or any combination thereof. Each possibility represents a separate embodiment of the present invention. In some embodiments, the cancer cell expresses CEACAM1, PD-L1, or both. Each possibility represents a separate embodiment of the present invention. In some embodiments, the cancer cell expresses CEACAM1, PD-L2, or both. Each possibility represents a separate embodiment of the present invention. In certain such embodiments, the cancer cell expresses CEACAM1 and PD-L1 and PD-L2.

In some embodiments, the cancer is selected from the group consisting of a melanoma, lymphoma, lung, thyroid, breast, colon, prostate, hepatic, bladder, renal, cervical, pancreatic, leukemia, myeloid, ovarian, uterus, sarcoma, biliary, and endometrial cells cancers. Each possibility represents a separate embodiment of the present invention. In some embodiments, the cancer is selected from the group consisting of a melanoma and lymphoma cancers. Each possibility represents a separate embodiment of the present invention. In some embodiments, the cancer is melanoma. In some embodiments, the cancer is lymphoma.

In some embodiments, the monoclonal antibody to at least one of human PD-1, PD-L1 and PD-L2 is capable of inhibiting or blocking the interaction between human PD-1 and its ligands. Each possibility represents a separate embodiment of the present invention.

In some embodiments, the method comprises administering to said patient a pharmaceutical composition comprising a monoclonal antibody to human CEACAM1 or an antigen-binding fragment thereof, and a pharmaceutical composition comprising a monoclonal antibody to human PD-1 or an antigen-binding fragment thereof. Each possibility represents a separate embodiment of the present invention.

In some embodiments, the method comprises administering to said patient a pharmaceutical composition comprising a monoclonal antibody to human CEACAM1 or an antigen-binding fragment thereof, and a pharmaceutical composition comprising a monoclonal antibody to human PD-L1 or an antigen-binding fragment thereof. Each possibility represents a separate embodiment of the present invention.

In some embodiments, the method comprises administering to said patient a pharmaceutical composition comprising a monoclonal antibody to human CEACAM1 or an antigen-binding fragment thereof, and a pharmaceutical composition comprising a monoclonal antibody to human PD-L2 or an antigen-binding fragment thereof. Each possibility represents a separate embodiment of the present invention.

In some embodiments of the method, the administration of two or more of the pharmaceutical compositions is done simultaneously. In some embodiments of the method, the administration of two or more of the pharmaceutical compositions is done sequentially. In some embodiments of the method, the monoclonal antibody to human PD-1 or an antigen-binding fragment thereof is administered before the monoclonal antibody to human CEACAM1 or an antigen-binding fragment thereof. In some embodiments of the method, the monoclonal antibody to human PD-1 or an antigen-binding fragment thereof is administered simultaneously with the monoclonal antibody to human CEACAM1 or an antigen-binding fragment thereof. In some embodiments of the method, the monoclonal antibody to human PD-1 or an antigen-binding fragment thereof is administered after the monoclonal antibody to human CEACAM1 or an antigen-binding fragment thereof. In some embodiments of the method, the administration of two or more of the pharmaceutical compositions is done simultaneously. In some embodiments of the method, the administration of two or more of the pharmaceutical compositions is done sequentially. In some embodiments of the method, the monoclonal antibody to human PD-L1 or an antigen-binding fragment thereof is administered before the monoclonal antibody to human CEACAM1 or an antigen-binding fragment thereof. In some embodiments of the method, the monoclonal antibody to human PD-L1 or an antigen-binding fragment thereof is administered simultaneously with the monoclonal antibody to human CEACAM1 or an antigen-binding fragment thereof. In some embodiments of the method, the monoclonal antibody to human PD-L1 or an antigen-binding fragment thereof is administered after the monoclonal antibody to human CEACAM1 or an antigen-binding fragment thereof. In some embodiments of the method, the monoclonal antibody to human PD-L2 or an antigen-binding fragment thereof is administered before the monoclonal antibody to human CEACAM1 or an antigen-binding fragment thereof. In some embodiments of the method, the monoclonal antibody to human PD-L2 or an antigen-binding fragment thereof is administered simultaneously with the monoclonal antibody to human CEACAM1 or an antigen-binding fragment thereof. In some embodiments of the method, the monoclonal antibody to human PD-L2 or an antigen-binding fragment thereof is administered after the monoclonal antibody to human CEACAM1 or an antigen-binding fragment thereof.

In some embodiments, the method described above further comprises the step of administering to said patient a pharmaceutical composition comprising a lymphocyte cell. In some embodiments of the method, the administration of the pharmaceutical composition comprising a lymphocyte cell is done simultaneously with at least one of the pharmaceutical compositions comprising the antibodies. In some embodiments of the method, the administration of the two or more pharmaceutical compositions is done sequentially.

In some embodiments, the lymphocyte cell is pre-incubated with a monoclonal antibody to human CEACAM1 or an antigen-binding fragment thereof or with a monoclonal antibody to human PD-1 or an antigen-binding fragment thereof prior to the administration. Each possibility represents a separate embodiment of the present invention. In certain such embodiments, the lymphocyte cell is pre-incubated with a monoclonal antibody to human CEACAM1 or an antigen-binding fragment thereof and a monoclonal antibody to human PD-1 or an antigen-binding fragment thereof prior to the administration. In other certain such embodiments, prior to the administration, the lymphocyte cell is pre-incubated with a monoclonal antibody to human PD-1 or an antigen-binding fragment thereof, and then incubated with a monoclonal antibody to human CEACAM1 or an antigen-binding fragment thereof.

In some embodiments, at least two different antibodies selected from the group consisting of anti-CEACAM1, anti-PD-1, anti-PD-L1 and anti-PD-L2 are comprised in at least two different pharmaceutical compositions. In some embodiments, at least one antibody selected from the group consisting of anti-CEACAM1, anti-PD-1, anti-PD-L1 and anti-PD-L2 and at least one lymphocyte cell are comprised in the same pharmaceutical composition.

In some embodiments, the kit comprises a pharmaceutical composition comprising a monoclonal antibody to human CEACAM1 or an antigen-binding fragment thereof, and a pharmaceutical composition comprising a monoclonal antibody to human PD-1 or an antigen-binding fragment thereof. In some embodiments, the kit comprises a pharmaceutical composition comprising a monoclonal antibody to human CEACAM1 or an antigen-binding fragment thereof, and a pharmaceutical composition comprising a monoclonal antibody to human PD-L1 or an antigen-binding fragment thereof. In some embodiments, the kit comprises a pharmaceutical composition comprising a monoclonal antibody to human CEACAM1 or an antigen-binding fragment thereof, and a pharmaceutical composition comprising a monoclonal antibody to human PD-L2 or an antigen-binding fragment thereof.

In certain embodiments, each pharmaceutical composition comprising an antibody or an antigen-binding fragment thereof is contained in a separate container within the kit.

In certain embodiments, the kit further comprises a pharmaceutical composition comprising a lymphocyte cell. In certain such embodiments, the kit comprises a pharmaceutical composition comprising the lymphocyte cell and the monoclonal antibody to human CEACAM1 or an antigen-binding fragment thereof or the monoclonal antibody to human PD-1 or an antigen-binding fragment thereof. Each possibility represents a separate embodiment of the present invention. In certain such embodiments, the kit comprises a pharmaceutical composition comprising the lymphocyte cell and the monoclonal antibody to human CEACAM1 or an antigen-binding fragment thereof. In certain such embodiments, the kit comprises a pharmaceutical composition comprising the lymphocyte cell and the monoclonal antibody to human PD-1 or an antigen-binding fragment thereof. In certain embodiments, the kit further comprises instructions for use of the kit.

BRIEF DESCRIPTION OF THE DRAWINGS

FIG. 7A-B. Treatment with anti-CEACAM1 antibodies increases PD-L1 expression on target cancer cells. NK cells (NK92MI) were incubated with or without a monoclonal antibody to human CEACAM1 (CM-24) (10 μg/ml), followed by the addition of human melanoma cells (SK-MEL28). The cells were incubated for 24, 48 and 72 hours and PD-L1 levels were measured at each time point by FACS analysis. A. Mean ratio of anti-PD-L1 compared to an appropriate isotype control for the indicated treatments at the different time points. B. Representative FACS analysis of PD-L1 expression levels after 48 hours.

DETAILED DESCRIPTION OF THE INVENTION

Figure 1A:
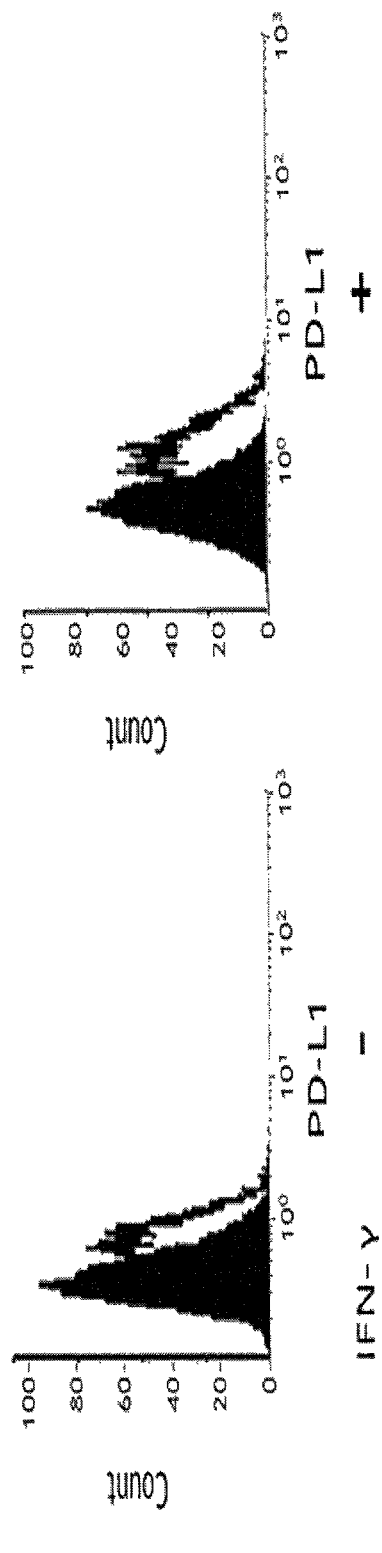
FIG. 1A-B. Human melanoma cells express CEACAM1 and PD-L1 upon IFN-γ activation. MALME 3M cells were incubated with IFN-γ for 24 hours, and analyzed by FACS with a PE-conjugated anti-PD-L1 antibody (empty histogram) or isotype control matched antibody (full histograms) (A), or with a PE-conjugated a monoclonal antibody to human CEACAM1 (empty histogram) or isotype control matched antibody (full histograms) (B).

The present invention stems from the surprising finding that combinations of anti-CEACAM1 antibodies and antibodies directed to disrupt the binding of PD-1 to its natural ligands, PD-L1 and PD-L2, significantly elevated the cytotoxicity of lymphocyte cells, such as tumor-infiltrating-lymphocyte (TIL) cells and lymphokine-activated killer (LAK) cells, toward different types of cancer. It was further surprisingly found that step-wise pre-incubation of the lymphocyte cells with these antibodies, rather than concurrent incubation, maximizes the lymphocytes' cytotoxicity. It was also found that the expression of CEACAM1 and PD-Ligands on cancer cells is interrelated, as binding of anti- CEACAM1 antibodies to the cancer cells increases PD-L1 expression. Further, it was found that such antibody combinations significantly attenuate the progression of established tumors in an immuno-competent murine model, assumingly exploiting the mice' natural lymphocyte milieu.

Without being bound to any theory or mechanism, it is hypothesized, according to the findings of the present invention, that lymphocytes expressing CEACAM1 and/or PD-1 can be substantially suppressed by interactions with their corresponding ligands, CEACAM1 and/or PD-L1 and/or PD-L2, which are presented e.g. by cancer cells. On the other hand, when these suppressive interactions are blocked, these lymphocytes may become cytotoxic toward these cancer cells upon activation and lead to killing of the malignant cells.

The present invention thus provides pharmaceutical compositions directed to obstruct two major immuno-suppressive homotypic interactions, CEACAM1$^{lymphocyte}$/CEACAM1$^{cancer\ cell}$, and PD-1$^{lymphocyte}$/PD-Ligand$^{cancer\ cell}$ and to increase the level of anti-cancer cytotoxic cells within the body of a patient diagnosed with cancer. Without being limited to any theory or mechanism, it is hypothesized that the compositions of the present invention generate a "two-punch" combination, in which the level of anti-cancer cytotoxic lymphocytes within the cancer patient is raised, while their cytotoxicity is maintained by protective interaction with anti-CEACAM1 antibodies and/or anti-PD-1/PD-L1/PD-L2 antibodies, bound to CEACAM1 and/or PD-1 molecules presented by the lymphocyte themselves, the CEACAM1/PD-L1/PD-L2 molecules presented by the cancer cells, or both.

The present invention thus provides, in one aspect, a pharmaceutical composition comprising a monoclonal antibody to human carcinoembryonic antigen-related cell adhesion molecule 1 (CEACAM1) or an antigen-binding fragment thereof, and a pharmaceutical composition comprising a monoclonal antibody to at least one of human programmed cell death protein 1 (PD-1), PD-L1 and PD-L2 or an antigen-binding fragment thereof, for use in treatment of cancer by separate administration.

The present invention further provides, in another aspect, a pharmaceutical composition comprising a monoclonal antibody to human-carcinoembryonic antigen-related cell adhesion molecule 1 (CEACAM1) or an antigen-binding fragment thereof, and a pharmaceutical composition comprising a monoclonal antibody capable of inhibiting or blocking the interaction between human programmed cell death protein 1 (PD-1) and its ligands or an antigen-binding fragment thereof, for use in treatment of cancer by separate administration.

The present invention further provides, in another aspect, a monoclonal antibody to human-carcinoembryonic antigen-related cell adhesion molecule 1 (CEACAM1) or an antigen-binding fragment thereof, and a monoclonal antibody capable of inhibiting or blocking the interaction between human programmed cell death protein 1 (PD-1) and its ligands or an antigen-binding fragment thereof, for use in treatment of cancer by separate administration.

The present invention further provides, in yet another aspect, a method for treating a patient having cancer, comprising administering to the patient a pharmaceutical composition comprising a monoclonal antibody to human CEACAM1 or an antigen-binding fragment thereof, and a pharmaceutical composition comprising a monoclonal antibody to at least one of human PD-1, PD-L1 and PD-L2 or an antigen-binding fragment thereof, thereby treating the cancer.

More, the present invention provides, in another aspect, a kit comprising a pharmaceutical composition comprising a monoclonal antibody to human CEACAM1 or an antigen-binding fragment thereof, and a pharmaceutical composition comprising a monoclonal antibody to at least one of human PD-1, PD-L1 and PD-L2 or an antigen-binding fragment thereof.

The present invention provides, in another aspect, the kit described above, for use in treating cancer.

The term "separate administration" as used herein refers to different therapeutic agents such as antibodies being comprised in separate pharmaceutical compositions. In certain embodiments, the different therapeutic agents or the different pharmaceutical compositions are administered to cancer patients simultaneously or one after the other. Each possibility represents a separate embodiment of the invention. For example, by the phrase "a monoclonal antibody to human-CEACAM1, and a monoclonal antibody to human-PD-1, for use in treatment of cancer by separate administration" it is meant that the anti-CEACAM1 antibody is comprised in a composition which is different from the composition comprising the anti-PD-1 antibody.

The term "CEACAM1" is used to refer to the protein product of the CEACAM1 gene e.g., NP_001020083.1, NP_001703.2. In humans, 11 different CEACAM1 splice variants have been detected so far. Individual CEACAM1 isoforms differ with respect to the number of extracellular immunoglobulin-like domains (for example, CEACAM1 with four extracellular immunoglobulin-like domains is known as CEACAM1-4), membrane anchorage and/or the length of their cytoplasmic tail (for example, CEACAM1-4 with a long cytoplasmic tail is known as CEACAM1-4L and CEACAM1-4 with a short cytoplasmic tail is known as CEACAM1-4S). The N-terminal domain of CEACAM1 starts immediately after the signal peptide and its structure is regarded as IgV-type. For example, in CEACAM1 annotation P13688, the N-terminal IgV-type domain is comprised of 108 amino acids, from amino acid 35 to 142. This domain was identified as responsible for the homophilic binding activity (Watt et al., 2001, Blood. 98, 1469-79). All variants, including these splice variants are included within the term "CEACAM1".

The term "pharmaceutical composition" as used herein refers to a composition comprising at least one biologically active ingredient. Antibodies, antigen-binding fragments thereof, and lymphocyte cells are non-limiting examples of biologically active ingredients.

The term "antibody" is used in the broadest sense and includes monoclonal antibodies (including full length or intact monoclonal antibodies), polyclonal antibodies, multivalent antibodies, multispecific antibodies (e.g., bispecific antibodies), immuno-modulatory agents, and antibody fragments of sufficient size to retain and exhibit the full antibody's desired biological activity.

The term "immuno-modulatory agent" or "immuno-modulatory protein" or "antibody fragment" as used interchangeably includes synthetic or genetically engineered proteins that act like an antibody by binding to a specific antigen to form a complex. For example, antibody fragments include isolated fragments consisting of the variable regions, such as the "Fv" fragments consisting of the variable regions of the heavy and light chains and recombinant single chain polypeptide molecules in which light and heavy variable regions are connected by a peptide linker ("scFv proteins"). The fragments may be constructed in different ways to yield multivalent and/or multi-specific binding forms. Antibody or antibodies according to the invention include intact antibodies, such as polyclonal antibodies or monoclonal antibodies (mAbs), as well as proteolytic fragments thereof such as the Fc, Fab or F(ab')$_2$ fragments. Further included within the scope of the invention are chimeric antibodies; human and humanized antibodies; recombinant and engineered antibodies, and fragments thereof.

An "a monoclonal antibody to human CEACAM1", "an antibody which recognizes CEACAM1", "an antibody against CEACAM1", or "an antibody to CEACAM1" is an antibody that binds to the CEACAM1 protein with sufficient affinity and specificity. Typically, a monoclonal antibody to human CEACAM1 is capable of binding CEACAM1 with a minimal affinity of about $10^{-8}$ or $10^{-9}$ M. Some of the monoclonal anti-CEACAM1 antibodies are capable of binding CEACAM3, 5 and/or 8 with a minimal affinity of about $5\times10^{-7}$ M. In certain embodiments, the monoclonal antibody to human CEACAM1 is capable of preventing, interfering or dissociating an interaction between CEACAM1 presented by lymphocytes and CEACAM1 presented by cancer cells.

A "neutralizing antibody" as used herein refers to a molecule having an antigen-binding site to a specific receptor or ligand target capable of reducing or inhibiting (blocking) activity or signaling through a receptor, as determined by in vivo or in vitro assays, as per the specification.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. Monoclonal Abs may be obtained by methods known to those skilled in the art. For example, the monoclonal antibodies to be used in accordance with the present invention may be made by the hybridoma method first described by Kohler et al., Nature 1975, 256, 495, or may be made by recombinant DNA methods (see, e.g., U.S. Pat. No. 4,816,567). The "monoclonal antibodies" may also be isolated from phage antibody libraries using the techniques described in Clackson et al., Nature 1991, 352, 624-628 or Marks et al., J. Mol. Biol., 1991, 222:581-597, for example.

The term "plurality" as used herein refers to two or more of the object specified.

The mAbs may be of any immunoglobulin class including IgG, IgM, IgE, IgA. A hybridoma producing a mAb may be cultivated in vitro or in vivo. High titers of mAbs can be obtained in vivo production where cells from the individual hybridomas are injected intraperitoneally into pristine-primed BALB/c mice to produce ascites fluid containing high concentrations of the desired mAbs. Monoclonal Abs of isotype IgM or IgG may be purified from such ascites fluids, or from culture supernatants, using column chromatography methods well known to those of skill in the art.

The term "antigenic determinant" or "epitope" according to the invention refers to the region of an antigen molecule that specifically reacts with particular antibody. An "antigen" is a molecule or a portion of a molecule capable of eliciting antibody formation and being bound by an antibody. An antigen may have one or more than one epitope. An antigen according to the present invention is a CEACAM1 protein or a fragment thereof.

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (fragment crystalline) domains. The antigen binding domains, Fab, include regions where the polypeptide sequence varies. The term F(ab')2 represents two Fab' arms linked together by disulfide bonds. The central axis of the antibody is termed the Fc fragment. Each heavy chain has at one end a variable domain (VH) followed by a number of constant domains (CH). Each light chain has a variable domain (VL) at one end and a constant domain (CL) at its other end, the light chain variable domain being aligned with the variable domain of the heavy chain and the light chain constant domain being aligned with the first constant domain of the heavy chain (CH1). The variable domains of each pair of light and heavy chains form the antigen-binding site. The domains on the light and heavy chains have the same general structure and each domain comprises four framework regions, whose sequences are relatively conserved, joined by three hypervariable domains known as complementarity determining regions (CDR1-3). These domains contribute specificity and affinity of the antigen-binding site. The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ) found in all antibody classes.

The terms "a monoclonal antibody to human CEACAM1", "monoclonal antibody to human PD-1", "anti-PD-L1 antibody" and "anti-PD-L2 antibody" as used herein refer to full immunoglobulin molecules, e.g. IgMs, IgDs, IgEs, IgAs or IgGs, antigen-binding-domains of such immunoglobulin molecules, e.g. Fab-fragments, Fab'-fragments, F(ab)2-fragements, chimeric F(ab)$_2$ or chimeric Fab' fragments, chimeric Fab-fragments or isolated VH- or CDR-regions, and known isoforms and modifications of immunoglobulins, e.g. single-chain antibodies or single chain Fv fragments (scAB/scFv) or bispecific antibody constructs, capable of binding to their indicated targets. The terms "anti-human-CEACAM1 antibody", "anti-human-PD-1 antibody", "monoclonal antibody to human PD-L1" and "monoclonal antibody to human PD-L2" as used herein refer to antibodies capable of binding to their indicated targets, wherein these targets are of human origin.

The terms "antigen-binding fragment of an antibody" and "antigen-binding fragment" as interchangeably used herein, refer to one or more fragments of an antibody that retains the ability to bind specifically to the disclosed antigen. For example, the antigen-binding fragment may include, but not limited to, Fab fragment, F(ab')2 fragment, scFv fragment, dAb fragment, CDR-containing fragment or isolated CDR. Therefore, an antigen-binding fragment of a monoclonal antibody to human CEACAM1 may be e.g. an Fab fragment of a monoclonal antibody to human CEACAM1, or any molecule which mimics the sequences and structure of such an Fab fragment, without being directly obtained from a monoclonal antibody to human CEACAM1, e.g. by chemical or enzymatic cleavage.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 1989, 341, 544-546) which consists of a VH domain; (vii) isolated CDR regions; (viii) F(ab')2 fragments, a bivalent fragment including two Fab' fragments linked by a disulphide bridge at the hinge region; (ix) single chain antibody molecules (e.g. single chain Fv; scFv) (Bird et al., Science 1988, 242, 423-426; and Huston et al., PNAS (USA) 1988, 85,5879-5883); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 1993, 90, 6444-6448); (xi) "linear antibodies" comprising a pair of tandem Fd segments (VH-CH1-VH-CH1) which, together with complementary light chain polypeptides, form a pair of antigen binding regions (Zapata et al. Protein Eng., 1995, 8, 1057-1062; and U.S. Pat. No. 5,641,870).

By the term "single chain variable fragment (scFv)" it is meant a fusion of the variable regions of the heavy and light chains of immunoglobulin, linked together with a short (usually serine, glycine) linker. Single chain antibodies can be single chain composite polypeptides having antigen binding capabilities and comprising amino acid sequences homologous or analogous to the variable regions of an immunoglobulin light and heavy chain (linked VH-VL or single chain Fv (scFv)). Both VH and VL may copy natural monoclonal antibody sequences or one or both of the chains may comprise a CDR-FR construct of the type described in U.S. Pat. No. 5,091,513, the entire contents of which are incorporated herein by reference. The separate polypeptides analogous to the variable regions of the light and heavy chains are held together by a polypeptide linker. Methods of production of such single chain antibodies, particularly where the DNA encoding the polypeptide structures of the VH and VL chains are known, may be accomplished in accordance with the methods described, for example, in U.S. Pat. Nos. 4,946,778, 5,091,513 and 5,096,815, the entire contents of each of which are incorporated herein by reference.

Single chain antibodies can be single chain composite polypeptides having antigen binding capabilities and comprising amino acid sequences homologous or analogous to the variable regions of an immunoglobulin light and heavy chain i.e. linked $V_H$-$V_L$ or single chain Fv (scFv).

The term "molecule having the antigen-binding portion of an antibody" as used herein is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, Fab mini-antibodies (see WO 93/15210, WO 96/13583, WO 96/37621, the entire contents of which are incorporated herein by reference), dimeric bispecific mini-antibodies (see Muller et al., 1998) and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

The term "antigen" as used herein refers to a molecule or a portion of a molecule capable of eliciting antibody formation and/or being bound by an antibody. An antigen may have one or more than one epitope. For example, the proteins CEACAM1, PD-1, PD-L1 and/or PD-L2 are each considered an antigen by the present invention. In preferred embodiments, the antigens are human antigens.

The term "antibody capable of inhibiting or blocking the interaction between PD-1 and its ligands" as used herein refers to any antibody or antigen-binding fragment thereof which interferes, inhibits, decreases, eliminates or prevents an interaction between a PD-1 molecule, e.g. presented by a lymphocyte cell, and a PD-L1 and/or a PD-L2 molecule, e.g. presented by a cancer cell, optionally by chemically and/or physically interacting with PD-1 and/or PD-L1 and/or PD-L2.

The term "treating cancer" as used herein, refers to administering therapeutic effective amounts of agents such as antibodies and/or lymphocyte cells to a patient diagnosed with cancer, to inhibit the further growth of malignant cells in the patient, to inhibit the spread of the malignant cells in the patient, and/or to cause the death of malignant cells in the patient. Thus, in certain embodiments, treating cancer means attenuating tumor progression, inhibiting the spread of the malignant cells in the patient, causing the death of malignant cells in the patient and any combination thereof. Each possibility represents a separate embodiment of the invention. In certain embodiments, treating cancer means attenuating tumor progression, causing the death of malignant cells in the patient, or both.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include melanoma, lung, thyroid, breast, colon, prostate, hepatic, bladder, renal, cervical, pancreatic, leukemia, lymphoma, myeloid, ovarian, uterus, sarcoma, biliary, or endometrial cancer.

The term "anti-neoplastic composition" refers to a composition useful in treating cancer comprising at least one active therapeutic agent capable of inhibiting or preventing tumor growth or function, and/or causing destruction of tumor cells. Therapeutic agents suitable in an anti-neoplastic composition for treating cancer include, but not limited to, chemotherapeutic agents, radioactive isotopes, toxins, cytokines such as interferons, and antagonistic agents targeting cytokines, cytokine receptors or antigens associated with tumor cells.

The term "kit" as used herein, refers to a combination of reagents and other materials. It is contemplated that the kit may include reagents such as antibodies, antibody mixtures, buffers, diluents and other aqueous solutions, and/or one or more storage vials or other containers. It is not intended that the term "kit" be limited to a particular combination of reagents and/or other materials.

The present invention also provides pharmaceutical compositions directed to simultaneously obstruct two major immuno-suppressive interactions: $CEACAM1^{lymphocyte}/CEACAM1^{cancer\ cell}$ and $PD-1^{lymphocyte}/PD-Ligand^{cancer\ cell}$. Thus, in some embodiments, the pharmaceutical compositions comprise a monoclonal antibody to human CEACAM1 or an antigen-binding fragment thereof and a monoclonal antibody to human PD-1 or an antigen-binding fragment thereof. Each possibility represents a separate embodiment of the invention. In some embodiments, the pharmaceutical compositions comprise a monoclonal antibody to human CEACAM1 or an antigen-binding fragment thereof and a monoclonal antibody to human PD-L1 or an antigen-binding fragment thereof. Each possibility represents a separate embodiment of the invention. In some embodiments, the pharmaceutical compositions comprise a monoclonal antibody to human CEACAM1 or an antigen-binding fragment thereof and a monoclonal antibody to human PD-L2 or an antigen-binding fragment thereof. Each possibility represents a separate embodiment of the invention. In some embodiments, the pharmaceutical compositions comprise a monoclonal antibody to human CEACAM1 or an antigen-binding fragment thereof, a monoclonal antibody to human PD-1 or an antigen-binding fragment thereof, and a monoclonal antibody to human PD-L1 or an antigen-binding fragment thereof. Each possibility represents a separate embodiment of the invention. In some embodiments, the pharmaceutical compositions comprise a monoclonal antibody to human CEACAM1 or an antigen-binding fragment thereof, a monoclonal antibody to human PD-1 or an antigen-binding fragment thereof and a monoclonal antibody to human PD-L2 or an antigen-binding fragment thereof. Each possibility represents a separate embodiment of the invention.

In an aspect, the present invention provides a pharmaceutical composition comprising an anti-human-CEACAM1 monoclonal antibody or an antigen-binding fragment thereof, and a monoclonal antibody selected from the group consisting of an anti-human-PD-1 antibody or an antigen-binding fragment thereof, an anti-human-PD-L1 antibody or an antigen-binding fragment thereof, and an anti-human-PD-L2 antibody or an antigen-binding fragment thereof. In some embodiments, the pharmaceutical composition comprises a monoclonal antibody to human CEACAM1 or an antigen-binding fragment thereof and a monoclonal antibody to human PD-1 or an antigen-binding fragment thereof. Each possibility represents a separate embodiment of the invention. In some embodiments, the pharmaceutical composition comprises a monoclonal antibody to human CEACAM1 or an antigen-binding fragment thereof and a monoclonal antibody to human PD-L1 or an antigen-binding fragment thereof. Each possibility represents a separate embodiment of the invention. In some embodiments, the pharmaceutical composition comprises a monoclonal antibody to human CEACAM1 or an antigen-binding fragment thereof and a monoclonal antibody to human PD-L2 or an antigen-binding fragment thereof. Each possibility represents a separate embodiment of the invention. In some embodiments, the pharmaceutical composition comprises a monoclonal antibody to human CEACAM1 or an antigen-binding fragment thereof, a monoclonal antibody to human PD-1 or an antigen-binding fragment thereof, and a monoclonal antibody to human PD-L1 or an antigen-binding fragment thereof. Each possibility represents a separate embodiment of the invention. In some embodiments, the pharmaceutical composition comprises a monoclonal antibody to human CEACAM1 or an antigen-binding fragment thereof, a monoclonal antibody to human PD-1 or an antigen-binding fragment thereof, and a monoclonal antibody to human PD-L2 or an antigen-binding fragment thereof. Each possibility represents a separate embodiment of the invention.

The phrase "the pharmaceutical compositions comprise antibody A and antibody B" refers to at least two separate pharmaceutical compositions, each one comprising at least one antibody which is different from the antibody comprised in the other pharmaceutical composition. The phrase "the pharmaceutical composition comprises" refers to a single pharmaceutical composition comprising at least two different antibodies.

Many monoclonal antibodies against the CEACAM1 protein are already known, all of which considered appropriate for use in the compositions and methods of the present inventions. Nevertheless, in some embodiments, the monoclonal antibody to human CEACAM1 is selected from the group consisting of CM-24, 26H7, 5F4, TEC-11, 12-140-4, 4/3/17, COL-4, F36-54, 34B1, YG-C28F2, D14HD11, b18.7.7, DU-ADM HEA81, B1.1, CLB-gran-10, F34-187, T84.1, B6.2, B1.13, YG-C94G7, 12-140-5, scFv DIATHIS1 and TET-2, antigen-binding fragments thereof, and any combination thereof. Each possibility represents a separate embodiment of the invention.

In a particular embodiment, the monoclonal antibody to human CEACAM1 is CM-24, antigen-binding fragments thereof, and any combination thereof. Each possibility represents a separate embodiment of the invention.

The CDR segments of CM-24 were identified using two different algorithm methods:

1. IMGT algorithm (Lefranc et al., 1999, Nucleic Acids Research, 27, 209-212);
2. KABAT algorithm (Wu T. T. and Kabat E. A., 1970, J. Exp. Med. 132, 211-250). Table 1 summarizes the determined CDR sequences using the two methods as well as the minimal consensus sequence and combined sequence of sequences identified using both methods.

TABLE 1

| | CDR sequences. | | | | | |
|---|---|---|---|---|---|---|
| | VH1 | VH2 | VH3 | VL1 | VL2 | VL3 |
| Consensus sequence | $X_1NNLX_2$* (SEQ ID NO: 1) | INPGSGDT (SEQ ID NO: 2) | GDYYGGFAV DY (SEQ ID NO: 3) | QDIGNY (SEQ ID NO: 4) | YTSR (SEQ ID NO: 5) | QQGKSLP (SEQ ID NO: 6) |

TABLE 1-continued

CDR sequences.

| | VH1 | VH2 | VH3 | VL1 | VL2 | VL3 |
|---|---|---|---|---|---|---|
| KABAT | NNLIE (SEQ ID NO: 7) | VINPGSGDTN YNEKFKG (SEQ ID NO: 8) | GDYYGGFAV DY (SEQ ID NO: 9) | RTSQDIGNYL N (SEQ ID NO: 10) | YTSRLHS (SEQ ID NO: 11) | QQGKSLP (SEQ ID NO: 12) |
| IMGT | GYAFTNNL (SEQ ID NO: 13) | INPGSGDT (SEQ ID NO: 14) | ARGDYYGGF AVDY (SEQ ID NO: 15) | QDIGNY (SEQ ID NO: 16) | YTSR (SEQ ID NO: 17) | QQGKSLPRT (SEQ ID NO: 18) |
| Combined sequence | GYAFTNNLIE (SEQ ID NO: 19) | VINPGSGDTN YNEKFKG (SEQ ID NO: 20) | ARGDYYGGF AVDY (SEQ ID NO: 21) | RTSQDIGNYL N (SEQ ID NO: 22) | YTSRLHS (SEQ ID NO: 23) | QQGKSLPRT (SEQ ID NO: 24) |

*wherein $X_1$ is absent or is Thr (T) and $X_2$ is absent or is Ile (I)

In some embodiments, the monoclonal antibody or fragment thereof which recognizes CEACAM1, comprises at least one heavy-chain CDR comprising a sequence selected from the group consisting of: SEQ ID NO: 1, SEQ ID NO: 2 and SEQ ID NO: 3, and at least one light-chain CDR comprising a sequence selected from the group consisting of: SEQ ID NO: 4, SEQ ID NO: 5 and SEQ ID NO: 6. Each possibility represents a separate embodiment of the invention.

In some embodiments, the monoclonal antibody or fragment thereof which recognizes CEACAM1, comprises at least two heavy-chain CDRs comprising a sequence selected from the group consisting of: SEQ ID NO: 1, SEQ ID NO: 2 and SEQ ID NO: 3, and at least one light-chain CDRs comprising a sequence selected from the group consisting of: SEQ ID NO: 4, SEQ ID NO: 5 and SEQ ID NO: 6. Each possibility represents a separate embodiment of the invention.

In some embodiments, the monoclonal antibody or fragment thereof which recognizes CEACAM1, comprises at least one heavy-chain CDR sequence of at least five consecutive amino acids derived from a sequence selected from the group consisting of: SEQ ID NO: 19, SEQ ID NO: 20 and SEQ ID NO: 21, and at least one light-chain CDR sequence of at least five amino acids derived from a sequence selected from the group consisting of: SEQ ID NO: 22, SEQ ID NO: 23 and SEQ ID NO: 24. Each possibility represents a separate embodiment of the invention.

In some embodiments, the binding site of the monoclonal antibody or fragment thereof which recognizes CEACAM1 consists of the six CDRs of SEQ ID NOs: 1, 2, 3, 4, 5, and 6. In some embodiments, the binding site of the monoclonal antibody or fragment thereof which recognizes CEACAM1 consists of the six CDRs of SEQ ID NOs: 7, 8, 9, 10, 11, and 12. In some embodiments, the binding site of the monoclonal antibody or fragment thereof which recognizes CEACAM1 consists of the six CDRs of SEQ ID NOs: 13, 14, 15, 16, 17, and 18. In some embodiments, the binding site of the monoclonal antibody or fragment thereof which recognizes CEACAM1 consists of the six CDRs of SEQ ID NOs: 19, 20, 21, 22, 23, and 24.

In certain embodiments, the monoclonal antibody or an antigen-binding fragment thereof which recognizes human CEACAM1 comprises a heavy-chain CDR1 comprising a sequence set forth in SEQ ID NO: 1, a heavy-chain CDR2 comprising a sequence set forth in SEQ ID NO: 2, a heavy-chain CDR3 comprising a sequence set forth in SEQ ID NO: 3, a light-chain CDR1 comprising a sequence set forth in SEQ ID NO: 4, a light-chain CDR2 comprising a sequence set forth in SEQ ID NO: 5 and a light-chain CDR3 comprising a sequence set forth in SEQ ID NO: 6, and analogs and derivatives thereof.

In certain embodiments, the monoclonal antibody or an antigen-binding fragment thereof which recognizes human CEACAM1 comprises a heavy chain CDR1 having the sequence set forth in SEQ ID NO: 7, heavy chain CDR2 having the sequence set forth in SEQ ID NO: 8 and heavy chain CDR3 having the sequence set forth in SEQ ID NO: 9. In certain embodiments, the monoclonal antibody or an antigen-binding fragment thereof which recognizes human CEACAM1 comprises a heavy chain CDR1 having the sequence set forth in SEQ ID NO: 13, heavy chain CDR2 having the sequence set forth in SEQ ID NO: 14 and heavy chain CDR3 having the sequence set forth in SEQ ID NO: 15.

In certain embodiments, the monoclonal antibody or an antigen-binding fragment thereof which recognizes human CEACAM1 comprises a light chain CDR1 having the sequence set forth in SEQ ID NO: 10, light chain CDR2 having the sequence set forth in SEQ ID NO: 11 and light chain CDR3 having the sequence set forth in SEQ ID NO: 12. In certain embodiments, the monoclonal antibody or an antigen-binding fragment thereof which recognizes human CEACAM1 comprises a light chain CDR1 having the sequence set forth in SEQ ID NO: 16, light chain CDR2 having the sequence set forth in SEQ ID NO: 17, and light chain CDR3 having the sequence set forth in SEQ ID NO: 18.

In certain embodiments, the monoclonal antibody or an antigen-binding fragment thereof which recognizes human CEACAM1 comprises CDR sequences set forth in SEQ ID NOs: 13, 14, 15, 16, 17, and 18. In certain embodiments, the monoclonal antibody or an antigen-binding fragment thereof which recognizes human CEACAM1 comprises CDR sequences set forth in SEQ ID NOs: 7, 8, 9, 10, 11, and 12.

In certain embodiments, the monoclonal antibody or an antigen-binding fragment thereof which recognizes human CEACAM1 comprises a heavy chain variable domain sequence having a sequence set forth in SEQ ID NO: 25, or an analog or derivative thereof having at least 97% sequence identity with said heavy chain sequence. In certain embodiments, the monoclonal antibody or an antigen-binding fragment thereof which recognizes human CEACAM1 comprises a light chain variable domain sequence having a sequence set forth in SEQ ID NO: 26, or an analog or derivative thereof having at least 97% sequence identity with said light chain sequence. In certain embodiments, the monoclonal antibody or an antigen-binding fragment thereof which recognizes human CEACAM1 comprises a heavy chain variable domain having a sequence set forth in SEQ ID NO: 25 and a light chain variable domain having a sequence set forth in SEQ ID NO: 26, or an analog or derivative thereof having at least 97% sequence identity with the antibody or fragment sequence.

In certain embodiments, the monoclonal antibody or an antigen-binding fragment thereof which recognizes human CEACAM1 comprises:
  i. a framework sequence selected from the group consisting of: mouse IgG2a, mouse IgG2b, mouse IgG3, human IgG1, human IgG2, human IgG3; and
  ii. six CDRs having sequences set forth in SEQ ID NOs: 13, 14, 15, 16, 17, and 18; or six CDRs having sequences set forth in SEQ ID NOs: 7, 8, 9, 10, 11, and 12; and
analogs and derivatives thereof having at least 97% sequence identity with said CDR sequences, wherein the monoclonal antibody or fragment binds with an affinity of at least about $5\times10^{-7}$M to at least two CEACAM subtypes.

In certain embodiments, the monoclonal antibody or an antigen-binding fragment thereof which recognizes human CEACAM1 comprises human derived constant regions selected from the group consisting of: human IgG1, human IgG2, and human IgG3. In certain embodiments, the human or humanized monoclonal antibody or an antigen-binding fragment thereof which recognizes human CEACAM1 comprises a constant region subclass of human IgG1 subtype.

In certain embodiments, the human or humanized monoclonal antibody or an antigen-binding fragment thereof which recognizes human CEACAM1 comprises the six CDRs having sequences set forth in SEQ ID NOs: 13, 14, 15, 16, 17, and 18; or the six CDRs having sequences set forth in SEQ ID NOs: 7, 8, 9, 10, 11, and 12; and analogs and derivatives thereof having at least 95% sequence identity with said CDR sequences, wherein the monoclonal antibody binds with an affinity of at least about $10^{-8}$M to CEACAM1.

In certain embodiments, the human or humanized monoclonal antibody or an antigen-binding fragment thereof which recognizes human CEACAM1 comprises a heavy chain sequence set forth in SEQ ID NO: 27. In certain embodiments, the human or humanized monoclonal antibody or an antigen-binding fragment thereof which recognizes human CEACAM1 comprises a light chain sequence set forth in SEQ ID NO: 28. In certain embodiments, the human or humanized monoclonal antibody or an antigen-binding fragment thereof which recognizes human CEACAM1 comprises a heavy chain sequence set forth in SEQ ID NO: 27, and light chain sequence set forth in SEQ ID NO: 28.

In certain embodiments, the monoclonal antibody or an antigen-binding fragment thereof which recognizes human CEACAM1 comprises at least the antigen-binding portion, which is capable of binding the same epitope on the CEACAM1 molecule to which a monoclonal antibody having the six CDR sequences set forth in SEQ ID NOs: 7, 8, 9, 10, 11 and 12, or the six CDR sequences set forth in SEQ ID NOs: 13, 14, 15, 16, 17 and 18, binds. In certain embodiments, the monoclonal antibody or an antigen-binding fragment thereof is reactive with an epitope within residues 17-29 and 68-79 of human CEACAM1 having the sequences VLLLVHNLPQQLF (SEQ ID NO:32) and YPNASLLIQNVT (SEQ ID NO:33) respectively.

In certain embodiments, the monoclonal antibody or an antigen-binding fragment thereof is reactive with an epitope comprising at least four amino acids of the sequence VLLL-VHNLPQQLF (SEQ ID NO: 29). In certain embodiments, the monoclonal antibody or an antigen-binding fragment thereof is reactive with an epitope comprising amino acid residues within the sequences VLLLVHNLPQQLF (SEQ ID NO: 29) and YPNASLLIQNVT (SEQ ID NO: 30). In certain embodiments, the monoclonal antibody or an antigen-binding fragment thereof is reactive with an epitope within sequences VLLLVHNLPQQLF (SEQ ID NO: 29) and PNASLLI (SEQ ID NO: 31).

In some embodiments, the monoclonal antibody to human CEACAM1 or an antigen-binding fragment thereof is capable of binding with an affinity of at least about $10^{-8}$M to a human CEACAM1 protein. Each possibility represents a separate embodiment of the invention. In some embodiments, the monoclonal antibody to human CEACAM1 or an antigen-binding fragment thereof is capable of binding with an affinity of at least about $5\times10^{-7}$M to at least one of a human CEACAM3 and human CEACAM5 protein. Each possibility represents a separate embodiment of the invention.

Several monoclonal antibodies against the PD-1 protein are already known, all of which considered appropriate for use in the compositions and methods of the present inventions. Nevertheless, in some embodiments, the monoclonal antibody to human PD-1 is selected from the group consisting of MK-3475, AMP514, BMS-936558, CT-011, antigen-binding fragments thereof, and any combination thereof. Each possibility represents a separate embodiment of the invention.

Several monoclonal antibodies against the PD-L1 protein are already known, all of which considered appropriate for use in the compositions and methods of the present inventions. Nevertheless, in some embodiments, the monoclonal antibody to human PD-L1 is selected from the group consisting of MEDI-4736, BMS-936559, MSB0010718C, MPDL3280A, antigen-binding fragments thereof, and any combination thereof. Each possibility represents a separate embodiment of the invention. A non-limiting example of an antibody according to the present invention is AMP-224, also known as B7-DCIg, which is a fusion protein of PD-L1 soluble receptor and an antibody's Fc domain, described in PCT application publication Nos. WO/2010/027827 and WO/2011/066342.

Several monoclonal antibodies against the PD-L2 protein are already known, such as those previously disclosed in PCT application publication no. WO/2010/036959, all of which are considered appropriate for use in the compositions and methods of the present inventions.

When the process of developing a specific antibody involves generation in a non-human immune system (such as that in mice), the protein sequences of the antibodies produced are partially distinct from homologous antibodies occurring naturally in humans, and are therefore potentially immunogenic when administered to human patients.

Thus, to avoid immunogenicity when administered to a human patient, in some embodiments, the monoclonal antibody to human CEACAM1 is a human or humanized monoclonal antibody. Each possibility represents a separate embodiment of the invention. In some embodiments, the monoclonal antibody to human PD-1 is a human or humanized monoclonal antibody. Each possibility represents a separate embodiment of the invention. In some embodiments, the monoclonal antibody to human PD-L1 is a human or humanized monoclonal antibody. Each possibility represents a separate embodiment of the invention. In some embodiments, the monoclonal antibody to human PD-L2 is a human or humanized monoclonal antibody. Each possibility represents a separate embodiment of the invention.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo), for example in the CDRs. However, the term "human antibody", as used herein, is not intended to include antibodies in which CDR sequences derived from the germline of another mammalian species, such as a mouse, have been grafted onto human framework sequences. In certain embodiments, the term "human antibody" refers to an isolated human antibody, i.e. isolated from a human donor. In certain embodiments, the term "human antibody" refers to a human antibody isolated from a hybridoma cell line. In certain embodiments, the term "human antibody" refers to a recombinant human antibody, i.e. produced by recombinant DNA technology.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. Nature Biotechnology 1996 14,309-314; Sheets et al. PNAS (USA), 1998, 95, 6157-6162); Hoogenboom and Winter, J. Mol. Biol., 1991, 227, 381; Marks et al., J. Mol. Biol., 1991, 222, 581). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al, Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huszar, Intern. Rev. Immunol. 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., J. Immunol., 147 (1):86-95 (1991); and U.S. Pat. No. 5,750,373.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, L. D., et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "humanized antibody" as used herein refers is intended to include antibodies that have their CDRs (complementarity determining regions) derived from a non-human species immunoglobulin and the remainder of the antibody molecule derived mainly from a human immunoglobulin.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody comprises substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also comprises at least a portion of an immunoglobulin constant region (Fc), typically that of a human immunoglobulin. For further details, see Jones et al., Nature 1986, 321, 522-525; Riechmann et al., Nature 1988, 332, 323-329; and Presta, Curr. Op. Struct. Biol., 1992 2, 593-596.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, L. D., et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Without being bound to any mechanism or theory, it is suggested that the substantial anti-cancer cytotoxic effect demonstrated by the antibodies' combination of the present invention both in-vitro and in-vivo may be strengthen by exogenous lymphocyte cells. Thus, in certain embodiments, the pharmaceutical compositions described above further comprise a lymphocyte cell or a plurality of lymphocyte cells.

The term "lymphocyte cell" or "lymphocyte" as used herein refers to any one of a natural killer (NK) cell (usually involved in cell-mediated, cytotoxic innate immunity), a T cell (usually involved in cell-mediated, cytotoxic adaptive immunity), a B cell (usually involved in humoral, antibody-driven adaptive immunity), a plurality thereof and any combination thereof. Peripheral blood mononucleated (PBMC) cells, tumor-infiltrating-lymphocyte (TIL) cells and lymphokine-activated killer (LAK) cells (usually involved in tumor cells' killing) are also considered lymphocyte cells. Non-limiting examples of lymphocytes include cytotoxic lymphocytes (CTLs, CD8$^+$ or CD4$^+$), NK cells (CD2$^+$), and T helper cells (CD4$^+$).

The terms "lymphokine-activated killer (LAK) cell", "lymphokine-activated killer cell" and "LAK cell" are used interchangeably and refer to a lymphocyte cell that has been stimulated or activated to kill tumor cells, i.e. to become more cytotoxic toward tumor cells. As LAK cells may be produced from homogenous or heterogeneous cell populations, the terms above further refer to homogenous or heterogeneous cell populations, stimulated or activated to become more cytotoxic toward tumor cells. In specific embodiments, LAK cells are produced from PBMC cells by IL-2.

It has been formerly well established that known lymphocyte activating agents, such as IL-2, Interferon-γ (IFN-γ) and/or anti-CD3 monoclonal antibodies, are capable of transforming lymphocytes, such as PBMC cells, to become more cytotoxic, thereby producing a cell population termed "activated, cytotoxic lymphocyte cells", "activated lymphocyte cells", "cytotoxic lymphocyte cells" or "activated lymphocytes", both in vitro and in vivo. The present invention, and others, provides ample guidance for a person of average skill in the field as to how to activate PBMCs to produce diverse populations of activated, cytotoxic lymphocyte cells without adverse side effects. For example, Stephen E. Ettinghausen and coworkers have established that systemic administration of recombinant IL-2 stimulates in vivo lymphoid cell proliferation in tissues (Stephen E. Ettinghausen et al., The Journal of Immunology, 1985, Vol. 135, No. 2, pages 1488-1497), and that recombinant IL-2 stimulates in vivo proliferation of adoptively transferred LAK cells (Stephen E. Ettinghausen et al., The Journal of Immunology, 1985, Vol. 135, No. 5, pages 3623-3635). Joseph H. Phillips and coworkers have established that the continuous administration of 100,000 U IL-2/kg/q8 is sufficient to prime PBMC cells to become LAK cells in patients with advanced colon carcinoma, malignant melanoma or renal cell cancer (J. Clin. Oncol., 1987, Vol. 5, pp. 1933-1941). Cytokine Induced Killer (CIK) cells are in-vitro activated human CD8 T cells which have acquired non-specific anti tumoral cytotoxicity, thus representing a cell population with double T cell and NK cell phenotype. Due to their in-vivo intratumoral homing and lack of Graft versus Host (GVH) reactivity, CIK cells have been extensively used in cancer patients either in autologous or allogeneic contexts. M. Introna et al. (Immunology Letters, 2013, Vol. 155, pages 27-30) provides a summary of CIK cells' main biological features as well as their most prominent clinical results.

In some embodiments, the lymphocyte cell expresses CEACAM1, PD-1, or both. Each possibility represents a separate embodiment of the present invention. In certain such embodiments, the lymphocyte cell expresses CEACAM1 and PD-1.

In some embodiments, the lymphocyte cell is selected from the group consisting of a tumor-infiltrating-lymphocyte (TIL) cell, a lymphokine-activated killer (LAK) cell, a cytokine induced killer (CIK) cell, a T cell, a B cell, an NK cell, and any combination thereof. Each possibility represents a separate embodiment of the present invention. In certain such embodiments, the lymphocyte cell is selected from the group consisting of a tumor-infiltrating-lymphocyte (TIL) cell and a lymphokine-activated killer (LAK) cell. In certain such embodiments, the lymphocyte cell is a tumor-infiltrating-lymphocyte (TIL) cell or a plurality of TIL cells. In certain such embodiments, the lymphocyte cell is a lymphokine-activated killer (LAK) cell or a plurality of LAK cells.

Without being bound to any mechanism or theory, it is suggested that the desired anti-cancer cytotoxic effect demonstrated by the lymphocytes of the present invention in-vitro may be maximized by using activated lymphocyte cells. Thus, in certain embodiments, the lymphocyte cell is activated.

The term "activated" as used herein refers to any lymphocyte cell exhibiting a cytotoxic activity, e.g. against a cancer cell line such as human melanoma cells (MALME 3M or SKMEL28), or exhibiting elevated granzyme B production levels.

In some embodiments, the lymphocyte cell is cytotoxic to a cancer cell.

The term "cytotoxic" as used herein refers to an agent (such as a lymphocyte cell) which is harmful to a cell's (such as a cancer cell) structure and/or function. For example, when exposed to dysfunctional somatic cells, cytotoxic T lymphocytes (CTLs) release the cytotoxins perforin, granzymes, and granulysin. Through the action of perforin, granzymes enter the cytoplasm of the target cell and their serine protease function triggers the caspase cascade, which is a series of cysteine proteases that eventually lead to apoptosis (programmed cell death).

The compositions and methods provided by the present invention are demonstrated to be effective against several cancer types unrelated by origin. In some embodiments, the cancer cell expresses CEACAM1, PD-L1, PD-L2, or any combination thereof. Each possibility represents a separate embodiment of the present invention. In some embodiments, the cancer cell expresses CEACAM1, PD-L1, or both. Each possibility represents a separate embodiment of the present invention. In some embodiments, the cancer cell expresses CEACAM1, PD-L2, or both. Each possibility represents a separate embodiment of the present invention. In certain such embodiments, the cancer cell expresses CEACAM1 and PD-L1 and PD-L2.

In some embodiments, the cancer is selected from the group consisting of a melanoma, lymphoma, lung, thyroid, breast, colon, prostate, hepatic, bladder, renal, cervical, pancreatic, leukemia, myeloid, ovarian, uterus, sarcoma, biliary, and endometrial cells cancers. Each possibility represents a separate embodiment of the present invention. In some embodiments, the cancer is selected from the group consisting of a melanoma and lymphoma cancers. Each possibility represents a separate embodiment of the present invention. In some embodiments, the cancer is melanoma. In some embodiments, the cancer is lymphoma.

In some embodiments, the monoclonal antibody to at least one of human PD-1, PD-L1 and PD-L2 is capable of inhibiting or blocking the interaction between human PD-1 and its ligands. Each possibility represents a separate embodiment of the present invention.

As described above, the present invention provides a method utilizing pharmaceutical compositions directed to simultaneously obstruct two major immuno-suppressive interactions: CEACAM1$^{lymphocyte}$/CEACAM1$^{cancer\ cell}$ and PD-1$^{lymphocyte}$/PD-Ligand$^{cancer\ cell}$. Therefore, in some embodiments, the method comprises administering to said patient a pharmaceutical composition comprising a monoclonal antibody to human CEACAM1 or an antigen-binding fragment thereof, and a pharmaceutical composition comprising a monoclonal antibody to human PD-1 or an antigen-binding fragment thereof.

In some embodiments, the method comprises administering to said patient a pharmaceutical composition comprising a monoclonal antibody to human CEACAM1 or an antigen-binding fragment thereof, and a pharmaceutical composition comprising a monoclonal antibody to human PD-L1 or an antigen-binding fragment thereof.

In some embodiments, the method comprises administering to said patient a pharmaceutical composition comprising a monoclonal antibody to human CEACAM1 or an antigen-binding fragment thereof, and a pharmaceutical composition comprising a monoclonal antibody to human PD-L2 or an antigen-binding fragment thereof.

In some embodiments of the method, the monoclonal antibody to human PD-1 or an antigen-binding fragment thereof is administered before the monoclonal antibody to human CEACAM1 or an antigen-binding fragment thereof. In some embodiments of the method, the monoclonal antibody to human PD-1 or an antigen-binding fragment thereof is administered simultaneously with the monoclonal antibody to human CEACAM1 or an antigen-binding fragment thereof. In some embodiments of the method, the monoclonal antibody to human PD-1 or an antigen-binding fragment thereof is administered after the monoclonal antibody to human CEACAM1 or an antigen-binding fragment thereof. In some embodiments of the method, the administration of two or more of the pharmaceutical compositions is done simultaneously. In some embodiments of the method, the administration of two or more of the pharmaceutical compositions is done sequentially. In some embodiments of the method, the monoclonal antibody to human PD-L1 or an antigen-binding fragment thereof is administered before the monoclonal antibody to human CEACAM1 or an antigen-binding fragment thereof. In some embodiments of the method, the monoclonal antibody to human PD-L1 or an antigen-binding fragment thereof is administered simultaneously with the monoclonal antibody to human CEACAM1 or an antigen-binding fragment thereof. In some embodiments of the method, the monoclonal antibody to human PD-L1 or an antigen-binding fragment thereof is administered after the monoclonal antibody to human CEACAM1 or an antigen-binding fragment thereof. In some embodiments of the method, the monoclonal antibody to human PD-L2 or an antigen-binding fragment thereof is administered before the monoclonal antibody to human CEACAM1 or an antigen-binding fragment thereof. In some embodiments of the method, the monoclonal antibody to human PD-L2 or an antigen-binding fragment thereof is administered simultaneously with the monoclonal antibody to human CEACAM1 or an antigen-binding fragment thereof. In some embodiments of the method, the monoclonal antibody to human PD-L2 or an antigen-binding fragment thereof is administered after the monoclonal antibody to human CEACAM1 or an antigen-binding fragment thereof.

In some embodiments, the method described above further comprises the step of administering to said patient a pharmaceutical composition comprising a lymphocyte cell. In some embodiments of the method, the administration of the pharmaceutical composition comprising a lymphocyte cell is done simultaneously with at least one of the pharmaceutical compositions comprising the antibodies. In some embodiments of the method, the administration of the two or more pharmaceutical compositions is done sequentially.

It was surprisingly found that the binding of anti-CEACAM1 antibodies and anti-PD-1 antibodies to their respective targets on lymphocyte cells is somehow interrelated. Thus, in some embodiments, the lymphocyte cell is pre-incubated with a monoclonal antibody to human CEACAM1 or an antigen-binding fragment thereof or with a monoclonal antibody to human PD-1 or an antigen-binding fragment thereof prior to the administration. Each possibility represents a separate embodiment of the present invention. In certain such embodiments, the lymphocyte cell is pre-incubated with a monoclonal antibody to human CEACAM1 or an antigen-binding fragment thereof and a monoclonal antibody to human PD-1 or an antigen-binding fragment thereof prior to the administration. In other certain such embodiments, prior to the administration, the lymphocyte cell is pre-incubated with a monoclonal antibody to human PD-1 or an antigen-binding fragment thereof, and then incubated with a monoclonal antibody to human CEACAM1 or an antigen-binding fragment thereof.

The phrase "pre-incubated with" as used herein refers to the lymphocyte cell, the monoclonal antibody to human CEACAM1 or an antigen-binding fragment thereof and/or the monoclonal antibody to human PD-1 or an antigen-binding fragment thereof being comprised in the same pharmaceutical compositions in such conditions that allow one or both antibodies or antigen-binding fragments thereof to bind their targets presented by the lymphocyte cell in a specific manner.

The human leukocyte antigen (HLA) system is the locus of genes that encode for proteins on the surface of cells that are responsible for regulation of the immune system in humans. The HLA genes are the human versions of the major histocompatibility complex (MHC) genes that are found in most vertebrates. HLAs are routinely used to match a patient of a disease with a healthy donor for cell or organ transplant. The best transplant outcome happens when the patient's HLAs and the donor's HLAs closely match, preferably identical. The term "autologous lymphocyte cell" as used herein refers to a lymphocyte cell obtained or derived from a cancer patient, optionally expanded or incubated with anti-CEACAM1 antibodies or antigen-binding fragments thereof and/or anti-PD-1 antibodies or antigen-binding fragments thereof, and administered to the same cancer patient. The term "autologous lymphocyte cell" as used herein further refers to a lymphocyte cell obtained or derived from a human leukocyte antigen (HLA)-matching donor.

In some embodiments, at least two different antibodies selected from the group consisting of anti-CEACAM1, anti-PD-1, anti-PD-L1 and anti-PD-L2 are comprised in at least two different pharmaceutical compositions. In some embodiments, at least one antibody selected from the group consisting of anti-CEACAM1, anti-PD-1, anti-PD-L1 and anti-PD-L2 and at least one lymphocyte cell are comprised in the same pharmaceutical composition.

In some embodiments, the kit comprises a pharmaceutical composition comprising a monoclonal antibody to human CEACAM1 or an antigen-binding fragment thereof, and a pharmaceutical composition comprising a monoclonal antibody to human PD-1 or an antigen-binding fragment thereof. In some embodiments, the kit comprises a pharmaceutical composition comprising a monoclonal antibody to human CEACAM1 or an antigen-binding fragment thereof, and a pharmaceutical composition comprising a monoclonal antibody to human PD-L1 or an antigen-binding fragment thereof. In some embodiments, the kit comprises a pharmaceutical composition comprising a monoclonal antibody to human CEACAM1 or an antigen-binding fragment thereof, and a pharmaceutical composition comprising a monoclonal antibody to human PD-L2 or an antigen-binding fragment thereof.

In certain embodiments, each pharmaceutical composition comprising an antibody or an antigen-binding fragment thereof is contained in a separate container within the kit.

In certain embodiments, the kit further comprises a pharmaceutical composition comprising a lymphocyte cell. In certain such embodiments, the kit comprises a pharmaceutical composition comprising the lymphocyte cell and the monoclonal antibody to human CEACAM1 or an antigen-binding fragment thereof or the monoclonal antibody to human PD-1 or an antigen-binding fragment thereof. Each possibility represents a separate embodiment of the present invention. In certain such embodiments, the kit comprises a pharmaceutical composition comprising the lymphocyte cell and the monoclonal antibody to human CEACAM1 or an antigen-binding fragment thereof. In certain such embodiments, the kit comprises a pharmaceutical composition comprising the lymphocyte cell and the monoclonal antibody to human PD-1 or an antigen-binding fragment thereof. In certain embodiments, the kit further comprises instructions for use of the kit.

The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the appended claims.

EXAMPLES

Example 1—Human Melanoma Cells Express CEACAM1 and PD-L1 Upon IFN-γ Activation

Human melanoma cells (MALME 3M) were incubated with IFN-γ (2000 units/ml) for 24 hours, followed by FACS analysis with a PE-conjugated anti-PD-L1 antibody (clone 29E.2A3) or with PE-conjugated a monoclonal antibody to human CEACAM1 (CM-24, developed by cCAM Biotherapeutics). A similar assay was conducted for isotype control.

Figure 1B:
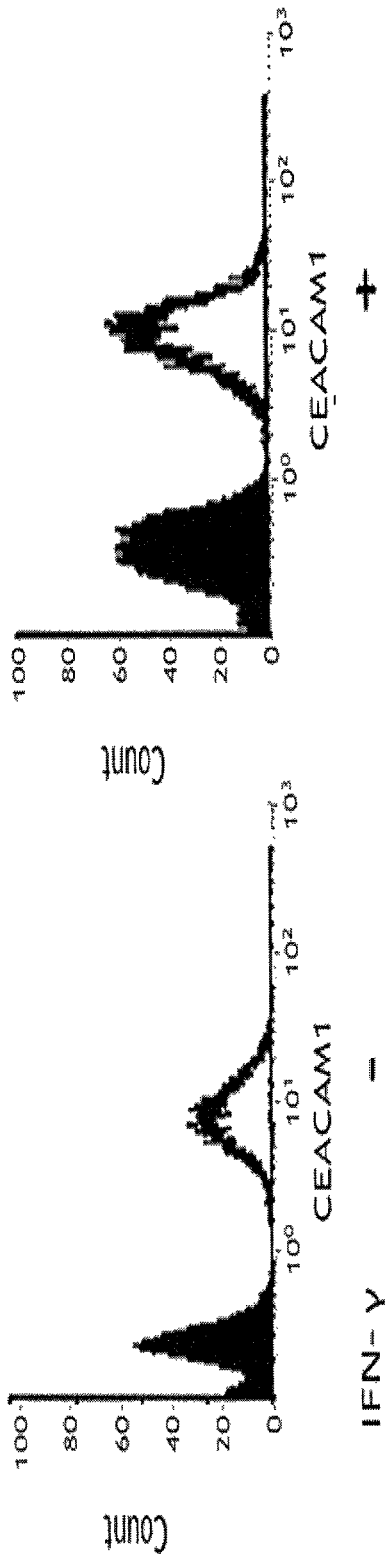

FIG. 1 demonstrates that human melanoma cells used in the experiments express both CEACAM1 and PD-L1.

Example 2—Human TIL Cells Express PD-1 and CEACAM1

Human TIL cells (tumor infiltrating lymphocytes expanded form patients #14 in Ella institute, Batch 14, TIL14) were stained with a monoclonal antibody to human PD-1 (clone E12.2H7) or with a PE-conjugated a monoclonal antibody to human CEACAM1 (CM-24) followed by FACS analysis. The expression of PD-1 (A) and CEACAM1 (B) compared to a matching isotype control is presented.

Figure 2A:
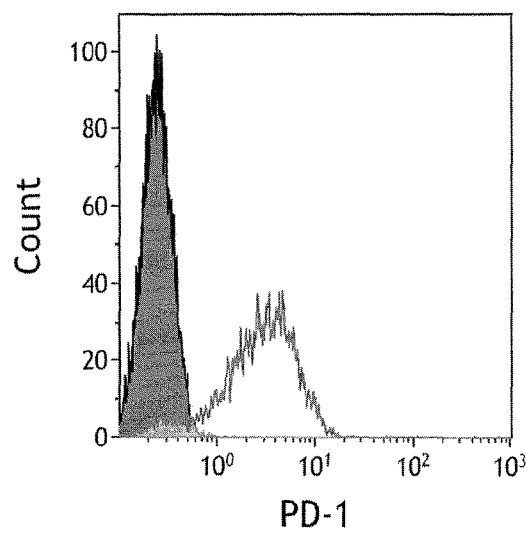
FIG. 2A-B. Human TIL cells express PD-1 and CEACAM1. TIL cells were stained with a monoclonal antibody to human PD-1 and analyzed by FACS. The expression of PD-1 (empty histogram) compared to a matching isotype control (full histogram) is presented (A), or with a PE-conjugated a monoclonal antibody to human CEACAM1 (empty histogram) or isotype control matched antibody (full histograms) (B).
Figure 2B:
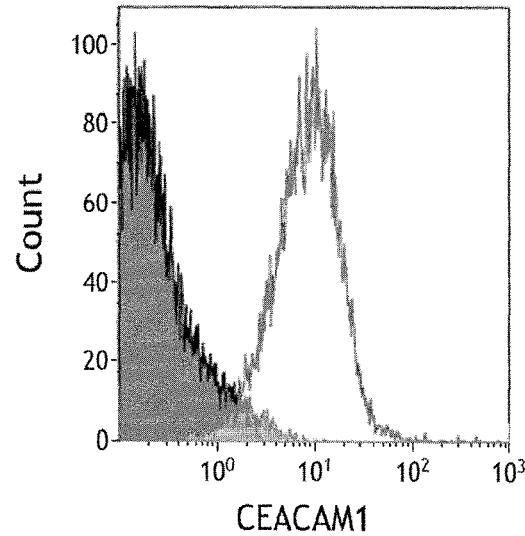

FIG. 2 demonstrates that the human TIL cells used in the experiments express both PD-1 and CEACAM1.

Example 3—Synergistic Effects of Anti-CEACAM1 and Anti-PD-1 Antibodies on the Cytotoxicity of Human TIL Cells Against Human Melanoma Cells Human melanoma cancer cells (MALME 3M) were grown in the presence of IFN-γ to induce PD-L1 expression. Human TIL cells (TIL14) were incubated with a monoclonal antibody to human CEACAM1 (CM-24) (0.01 μg/ml, 0.05 μg/ml, 0.1 μg/ml, 0.5 μg/ml), a monoclonal antibody to human PD-1 (clone E12.2H7) or with a combination of both antibodies (0.005, 0.025, 0.05 and 0.25 μg/ml of each antibody) for 30 minutes at 37° C.

Figure 3:
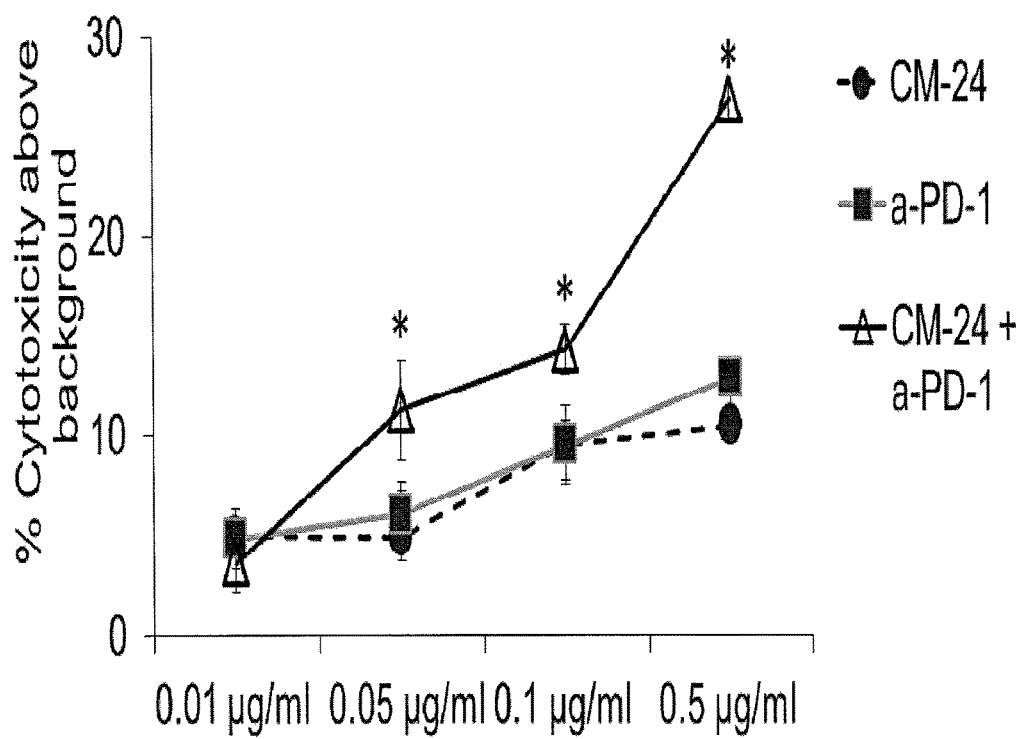
FIG. 3. Synergistic effects of anti-CEACAM1 and anti-PD-1 antibodies on the cytotoxicity of human TIL cells against human melanoma cells. Human melanoma cells were grown in the presence of IFN-γ to induce PD-1 expression. TIL cells were incubated with various concentrations of a monoclonal antibody to human CEACAM1 (dashed black line, sphere marker), a monoclonal antibody to human PD-1 (solid gray line, rectangular marker) or a combination of both antibodies (solid black line, triangle marker). The IFN-γ-treated melanoma cells were added for an overnight incubation. Results represent an average of % cytotoxicity ±SE as determined by classical LDH release assay from triplicate wells per treatment. *P<0.05 paired T-test compared to the monoclonal antibody to human CEACAM1 only.

IFN-γ-treated human melanoma cancer cells were added for overnight incubation, prior to cytotoxicity evaluation (FIG. 3). Results represent an average of % cytotoxicity ±SE as determined by classical LDH release assay from triplicate wells per treatment. *P<0.05 paired T-test compared to CM-24 only. The combination index (CI) was calculated to be ≤0.2, according to the following equation:

$$CI = \frac{(D)_1}{(D_x)_1} + \frac{(D)_2}{(D_x)_2} < 1 \rightarrow \text{synergism}$$

FIG. 3 demonstrates that both anti-CEACAM1 antibodies and anti-PD-1 antibodies were able to bind their respective targets on human lymphocytes such as TIL cells, and that this binding significantly increased the toxicity of the human TIL cells against human cancer cells over each monotherapy alone. Therefore, the data presented in FIG. 3 indicates that protecting lymphocytes from immuno-suppressive signals from target cancer cells results in substantial cytotoxicity toward these cancer cells.

Example 4—Synergistic Effects of Anti-CEACAM1 and Anti-PD-1 Antibodies on Granzyme B Levels and the Cytotoxicity of Human TIL Cells Against Human Melanoma Cells when Anti-PD-1 Antibodies are Added Prior to the Addition of Anti-CEACAM1 Antibodies Human melanoma cancer cells (MALME 3M) were grown in the presence of IFN-γ to induce PD-L1 expression. Human TIL cells (TIL14) were incubated with medium only (black), non-specific IgG antibody (0.8 μg/ml, white), various concentrations (0.05 μg/ml, 0.1 μg/ml, 0.2 μg/ml, 0.4 μg/ml, 0.8 μg/ml) of a monoclonal antibody to human CEACAM1 (CM-24), a monoclonal antibody to human PD-1 (clone E12.2H7) or a combination of both antibodies (0.05 μg/ml each, 0.1 μg/ml each, 0.2 μg/ml each, 0.4 μg/ml each, 0.8 μg/ml each).

Figure 4A:
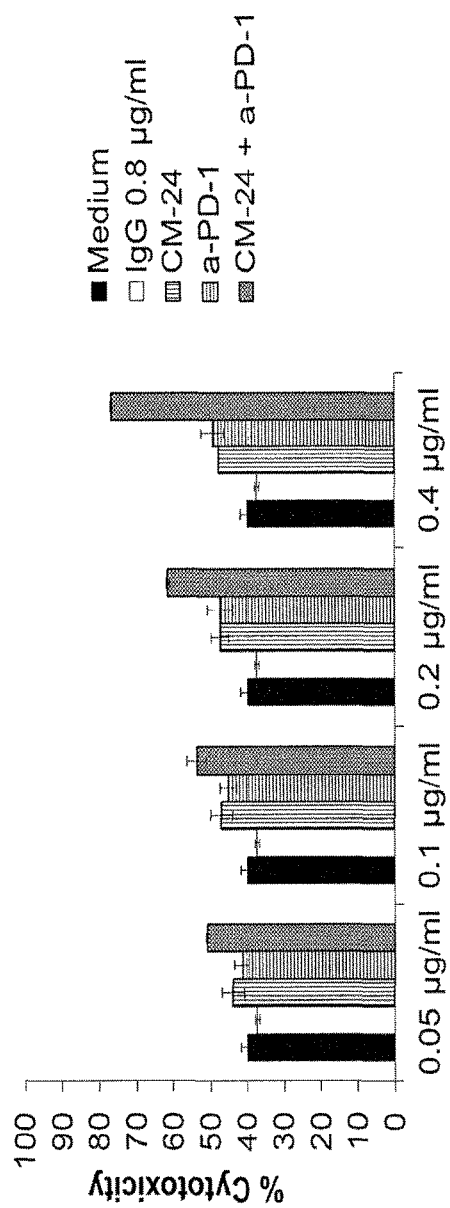
FIG. 4A-B. Synergistic effects of anti-CEACAM1 and anti-PD-1 antibodies on Granzyme B levels and the cytotoxicity of human TIL cells against human melanoma cells when anti-PD-1 antibodies are added prior to the addition of anti-CEACAM1 antibodies. Human melanoma cells were grown in the presence of IFN-γ to induce PD-L1 expression. Human TIL cells were incubated with medium only (black), non-specific IgG antibody (white), various concentrations of a monoclonal antibody to human CEACAM1 (vertical lines), a monoclonal antibody to human PD-1 (horizontal lines) or a combination of both antibodies (dots). The monoclonal antibody to human PD-1 was added first for 30 minutes at 37° C., followed by the addition of the monoclonal antibody to human CEACAM1. IFN-γ-treated MALME 3M cells were added for overnight incubation. (A) Results represent an average of % cytotoxicity ±SE as determined by classical LDH release assay from triplicate wells per treatment. *P≤0.05 paired T-test compared to a-PD-1 only. (B) Results represent Granzyme B levels ±SE as determined by commercial Granzyme B ELISA kit from triplicate wells per treatment.
Figure 4B:
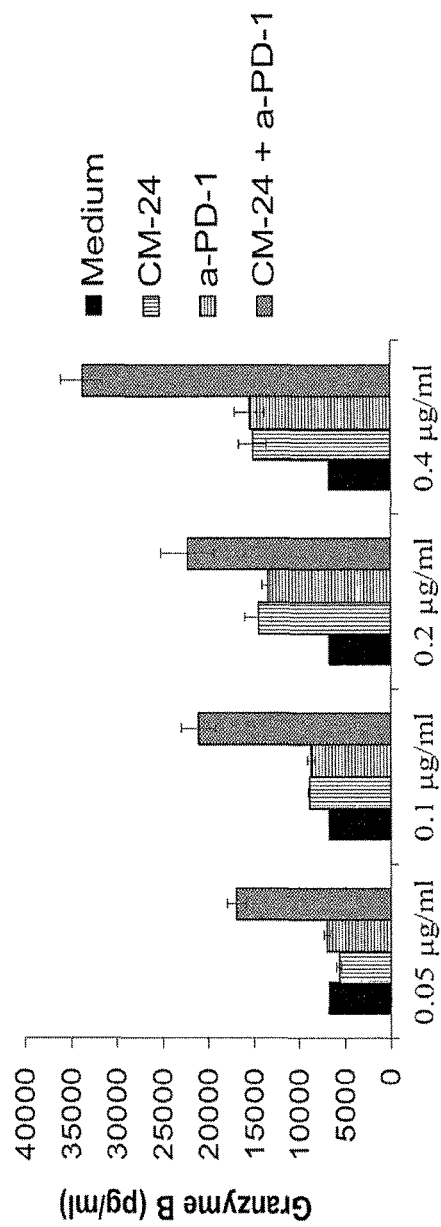

The monoclonal antibody to human PD-1 was added first for 30 minutes at 37° C., followed by the addition of the monoclonal antibody to human CEACAM1. IFN-γ-treated human melanoma cancer cells were added for overnight incubation, prior to cytotoxicity evaluation (FIG. 4A). The combination index (CI) was calculated to be 0.15. Results represent an average of % cytotoxicity ±SE as determined by classical LDH release assay from triplicate wells per treatment. *P<0.05 paired T-test compared to a-PD-1 only. In the same assay, the level of the cytotoxic protein granzyme B that is secreted upon cytotoxic cell activation was evaluated by commercial granzyme B ELISA Kit (FIG. 4B). Results represent average granzyme B level from triplicate wells per treatment.

FIG. 4 demonstrates that anti-CEACAM1 antibodies and anti-PD-1 antibodies are able to bind their respective targets on human lymphocytes such as TIL cells, and that this binding increases the granzyme B secretion and toxicity of the human TIL cells against human cancer cells. FIG. 4 further demonstrates that the binding of these antibodies to human TIL cells is somehow interrelated, warranting a further study of their binding mechanism. In similarity to the data presented in FIG. 3, FIG. 4 indicates again that protecting lymphocytes from immuno-suppressive signals from target cancer cells results in substantial cytotoxicity toward target cancer cells and suggests that timing could be a critical factor in the combined therapy.

Example 5—Synergistic Effects of Anti-CEACAM1 and Anti-PD-L1 Antibodies on Granzyme B Levels and the Cytotoxicity of Human TIL Cells Against Human Melanoma Cells when Anti-PD-L1 Antibodies are Added Prior to the Addition of Anti-CEACAM1 Antibodies Human melanoma cells (MALME 3M) were grown in the presence of IFN-γ to induce PD-L1 expression. Human TIL cells (TIL14) were incubated with medium only (black), non-specific IgG antibody (0.8 µg/ml, white), various concentrations (0.05 µg/ml, 0.1 µg/ml, 0.2 µg/ml, 0.4 µg/ml, 0.8 µg/ml) of a monoclonal antibody to human CEACAM1 (CM-24), a monoclonal antibody to human PD-L1 (clone 29E.2A3) or a combination of both antibodies (0.05 µg/ml each, 0.1 µg/ml each, 0.2 µg/ml each, 0.4 µg/ml each, 0.8 µg/ml each). The anti-PD-L1 antibody was added first for 30 minutes at 37° C., followed by the addition of the monoclonal antibody to human CEACAM1.

Figure 5A:
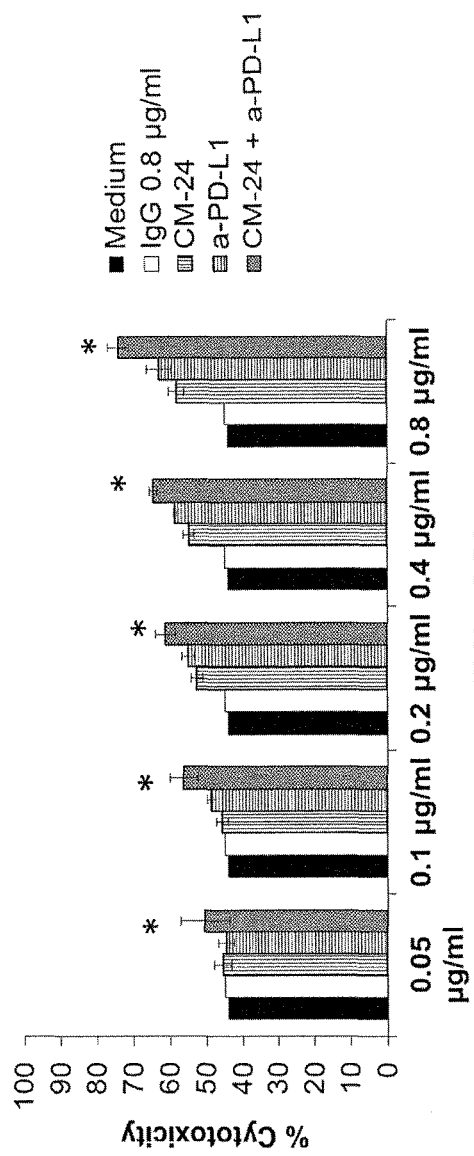
FIG. 5A-B. Synergistic effects of anti-CEACAM1 and anti-PD-L1 antibodies on Granzyme B levels and the cytotoxicity of human TIL cells against human melanoma cells when anti-PD-L1 antibodies are added prior to the addition of anti-CEACAM1 antibodies. Human melanoma cells were grown in the presence of IFN-γ to induce PD-L1 expression. Human TIL cells were incubated with medium only (black), non-specific IgG antibody (white), various concentrations of a monoclonal antibody to human PD-L1 (horizontal lines), a monoclonal antibody to human CEACAM1 (vertical lines) or a combination of both antibodies (dots). The anti-PD-L1 antibody was added first for 30 minutes at 37° C., followed by the addition of the monoclonal antibody to human CEACAM1. IFN-γ-treated MALME 3M cells were added for overnight incubation prior to cytotoxicity evaluation (A). Results represent an average of % cytotoxicity ±SE as determined by classical LDH release assay from triplicate wells per treatment. (B) Results represent Granzyme B levels ±SE as determined by commercial Granzyme B ELISA kit from triplicate wells per treatment. *P≤0.05 paired T-test compared to a-PD-L1 only.
Figure 5B:
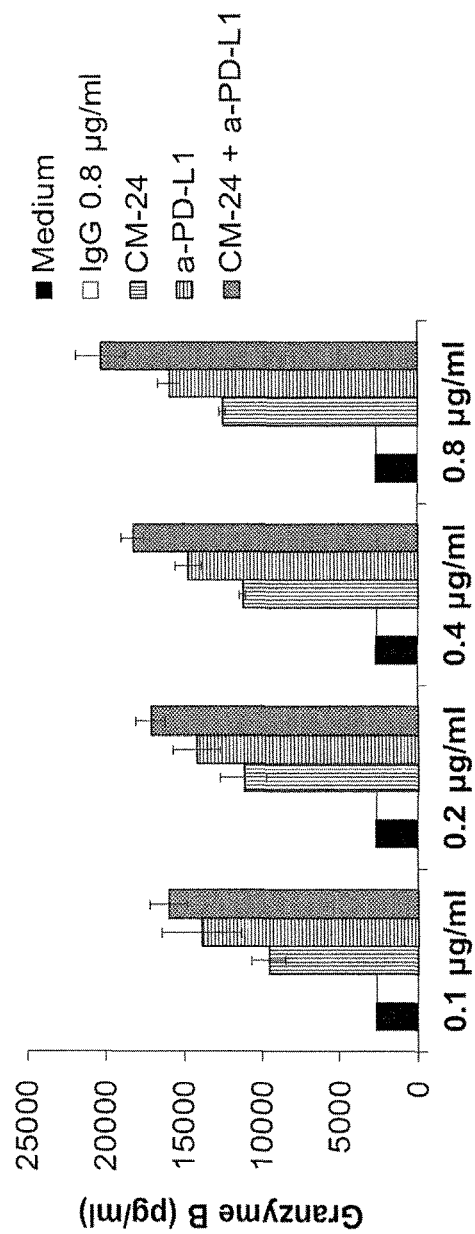

IFN-γ-treated human melanoma cancer cells were added for overnight incubation prior to cytotoxicity evaluation (FIG. 5A). The combination index (CI) was calculated to be 0.67. Results represent an average of % cytotoxicity ±SE as determined by classical LDH release assay from triplicate wells per treatment. *P≤0.05 paired T-test compared to a-PD-L1 only. In the same assay, the levels of the cytotoxic protein granzyme B that is secreted upon cytotoxic cell activation was evaluate by commercial granzyme B ELISA Kit (FIG. 5B). Results represent average granzyme B level from triplicate wells per treatment.

FIG. 5 demonstrates that anti-CEACAM1 antibodies and anti-PD-L1 antibodies are able to bind their respective targets on human lymphocytes (such as TIL cells) and on human cancer cells (such as melanoma cells), and that this binding increases the granzyme B secretion and toxicity of the human TIL cells against human cancer cells. FIG. 5 further demonstrates that blocking the PD-1/PD-L1 and CEACAM1/CEACAM1 interactions can result in synergistic affect. Therefore, the data presented in FIG. 5 indicates that protecting lymphocytes from the PD-1$^{lymphocyte}$/PD-Ligand$^{cancer\ cell}$ immuno-suppressive signal results in substantial cytotoxicity toward these cancer cells, regardless to the antigen targeted, either PD-1, PD-L1 or PD-L2.

Example 6—Synergistic Effects of Anti-CEACAM1 and Anti-PD-1 Antibodies on the Cytotoxicity of Human LAK Cells Against Human Melanoma Cells when Anti-PD-1 Antibodies are Added Prior to the Addition of Anti-CEACAM1 Antibodies Human melanoma cells (SKMEL28, CEACAM1 positive, PD-L1 positive) were grown in the presence of IFN-γ to induce PD-L1 expression. Human LAK (lymphokine-activated killer) cells generated by activation of PBMCs from a healthy human donor with IL-2 (500 units/ml) for 7 days were incubated with medium only (black), non-specific IgG antibody (0.8 µg/ml, white), various concentrations (0.05 µg/ml, 0.1 µg/ml, 0.2 µg/ml, 0.4 µg/ml, 0.8 µg/ml) of a monoclonal antibody to human CEACAM1 (CM-24), a monoclonal antibody to human PD-1 (clone E12.2H7) or a combination of both antibodies (0.05 µg/ml each, 0.1 µg/ml each, 0.2 µg/ml each, 0.4 µg/ml each, 0.8 µg/ml each). The monoclonal antibody to human PD-1 was added first for 30 minutes at 37° C., followed by the addition of the monoclonal antibody to human CEACAM1.

Figure 6:
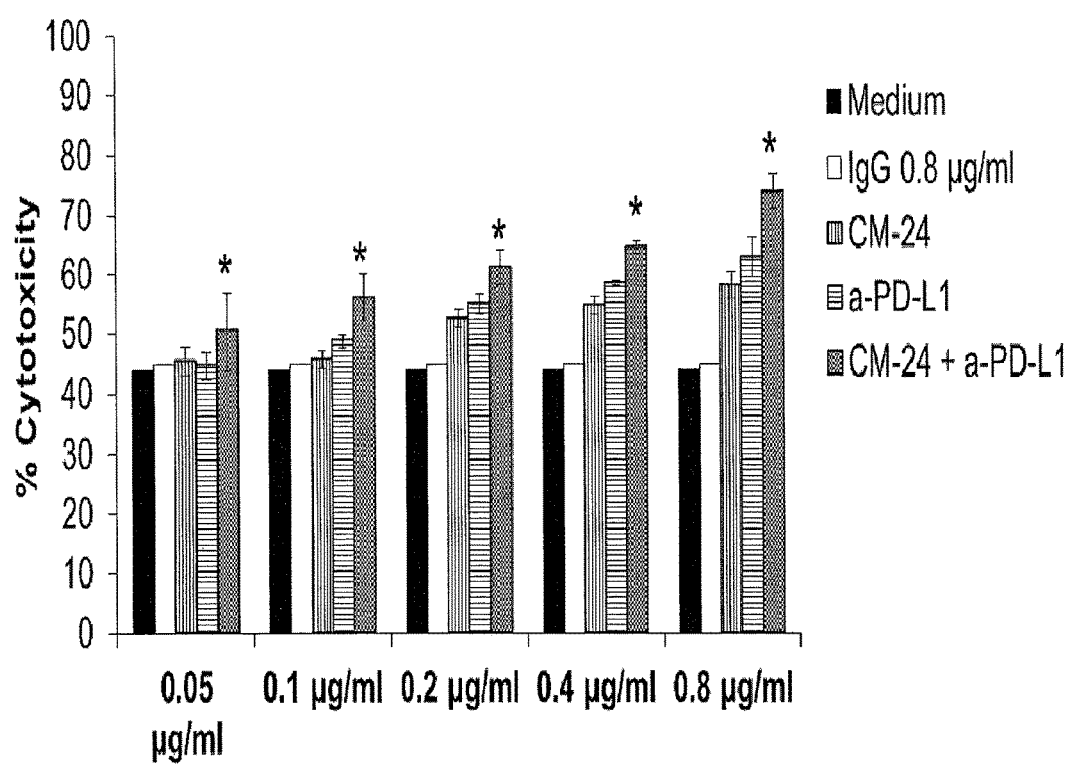
FIG. 6. Synergistic effects of anti-CEACAM1 and anti-PD-1 antibodies on the cytotoxicity of human LAK cells against human melanoma cells when anti-PD-1 antibodies are added prior to the addition of anti-CEACAM1 antibodies. Human melanoma cells were grown in the presence of IFN-γ to induce PD-L1 expression. Human LAK cells generated by activation of PBMCs from a healthy human donor with IL-2 were incubated with medium only (black), non-specific IgG antibody (white), various concentrations of a monoclonal antibody to human CEACAM1 (vertical lines), a monoclonal antibody to human PD-1 (horizontal lines) or a combination of both antibodies (dots). The monoclonal antibody to human PD-1 was added first for 30 minutes at 37° C., followed by the addition of the monoclonal antibody to human CEACAM1. IFN-γ-treated SKMEL28 cells were added for 24 hour incubation. Results represent an average of % cytotoxicity ±SE as determined by classical LDH release assay from triplicate wells per treatment. *P≤0.05 paired T-test compared to a-PD-1 only. Combination index was calculated as described above.

IFN-γ-treated human melanoma cells were added for 24 hour incubation, prior to cytotoxicity evaluation (FIG. 6). The combination index (CI) was calculated to be ≤0.2. Results represent an average of % cytotoxicity ±SE as determined by classical LDH release assay from triplicate wells per treatment. *P≤0.05 paired T-test compared to a-PD-1 only.

FIG. 6 demonstrates that anti-CEACAM1 antibodies and anti-PD-1 antibodies are able to bind their respective targets on activated human lymphocytes such as LAK cells, and that this binding increases the toxicity of the human LAK cells against human cancer cells. FIG. 6 further demonstrates that the binding of these antibodies to LAK cells is somehow interrelated, warranting a further study of their binding mechanism, and that this mechanism is present in variety of activated lymphocytes.

Example 7—Treatment with Anti-CEACAM1 Antibodies Increases PD-L1 Expression on Target Cancer Cells Human NK cells (NK92MI) were incubated with or without a monoclonal antibody to human CEACAM1 (10 µg/ml CM-24), followed by the addition of human melanoma cancer cells (SKMEL28). The cells were incubated for 24, 48 and 72 hours and PD-L1 levels were measured at each time point by FACS analysis. FIG. 7A illustrates the mean ratio levels of anti-PD-L1 compared to an appropriate isotype control for the indicated treatments at the different time points. B. Representative FACS analysis of PD-L1 levels after 48 hours.

FIG. 7 demonstrates that the expression of CEACAM1 and PD-L1 on cancer cells is indeed interrelated. The addition of anti-CEACAM1 antibodies results in increased PD-L1 expression on surviving cancer cells thus providing additional support for combined treatment with both agents. It is therefore may be beneficial to treat cancer by first administering anti CEACAM1 antibodies, and then further administering anti-PD-L1 and/or anti-PD-L2 antibodies, since the number of PD-L1 proteins on the cancer cells remains relatively high, making the cells more sensitive for anti PD-1/PD-L1 antibodies treatment, implying that the combinational therapy may improve the clinical outcome.

The data presented in Examples 4 to 6 demonstrates a surprising finding, according to which administration of different antibodies at separate times, rather than concurrently, maximizes the cytotoxic effect of lymphocytes against cancer cells. Without being bound to any theory or mechanism, this finding may be linked to another surprising finding of the present invention, according to which treatment with anti-CEACAM1 antibodies increases PD-L1 expression on target cancer cells. Hypothetically, this would support the need for a plurality of antibodies to obtain improved efficacy for cytotoxic lymphocytes. It may be envisioned that the administration of anti-PD-1 antibodies first blocks PD-1 molecules on lymphocytes, the later administration of anti-CEACAM1 antibodies blocks CEACAM1 molecules on lymphocytes and/or target cancer cells and increases expression of PD-1 ligands on target cancer cells. However, since PD-1 molecules on lymphocytes are already blocked, the elevated expression levels of PD-1 ligands on target cancer cells do not prevent lymphocytes from efficiently exerting their full cytotoxic potential.

Example 8—Synergistic Effects of Anti-CEACAM1 and Anti-PD-1 Antibodies on Tumor Progression in Immuno-Competent Mice Murine lymphoma cells ($5*10^6$, A20) were allografted into the abdomen of Balb/C mice by sub-cutaneous injection on Day 1. On day 10, tumors reached an average volume of 45 mm$^3$, and mice were randomized into 4 separate groups (11-12 mice per group), and intravenously administered with either PBS (FIG. 8, dashed black line, empty circles), CC-1 (anti murine CEACAM1 antibody, 6 mg/kg, FIG. 8, solid gray line, gray rectangles), PRM-1 (anti murine PD-1 antibody, 6 mg/kg, FIG. 8, solid gray line, gray triangles) or a combination of CC-1 and PRM-1 (6 mg/kg each, FIG. 8, solid black line, black spheres). Treatments were repeated on days 15 and 20. Experiment was terminated on Day 22. The effect of a monoclonal antibody to human CEACAM1 alone, a monoclonal antibody to human PD-1 alone, and a combination of both antibodies on tumor growth inhibition was followed.

Immuno-competent Balb/C mice were selected for this experiment to allow evaluation of anti-murine-CEACAM1 and anti-murine-PD-1 antibodies' biological activity in mice with intact immune system and to evaluate the entire immune system reaction against the murine cancer cells. As a whole, this model simulates therapies in humans, in which cancer patients would receive combinations of anti-human-CEACAM1 and anti-human-PD-1/PD-L1/PD-L2 antibodies. Without being bound to any theory or mechanism, it is hypothesized that a combination of anti-CEACAM1 and anti-PD-1/PD-L1/PD-L2 antibodies would prohibit cancer cells to circumvent the activation and cytotoxicity of the patient's immune system, thus producing a significant anti-cancer response.

Figure 8:
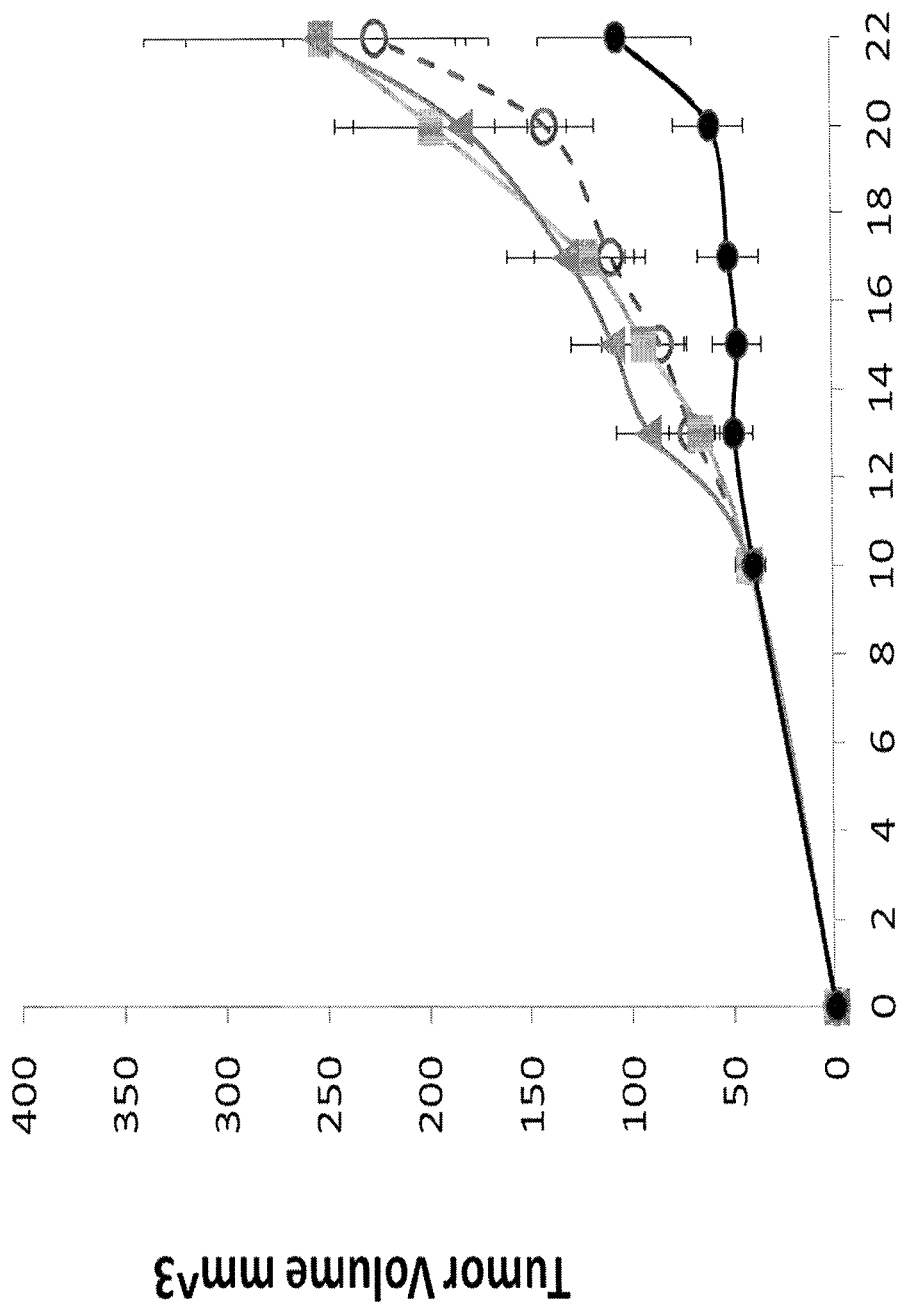
FIG. 8. Synergistic effects of anti-CEACAM1 and anti-PD-1 antibodies on tumor progression in immuno-competent mice. Murine lymphoma cells were implanted subcutaneously in the abdomen of BALB/C mice (Day 1). On days 10, 15 and 20, mice were intravenously administered with either PBS (dashed black line, empty circles), an anti-murine CEACAM1 antibody (solid gray line, gray rectangles), an anti-murine PD-1 antibody (solid gray line, gray triangles) or a combination of both antibodies (solid black line, black spheres). Experiment was terminated on Day 22.
Figure 9A:
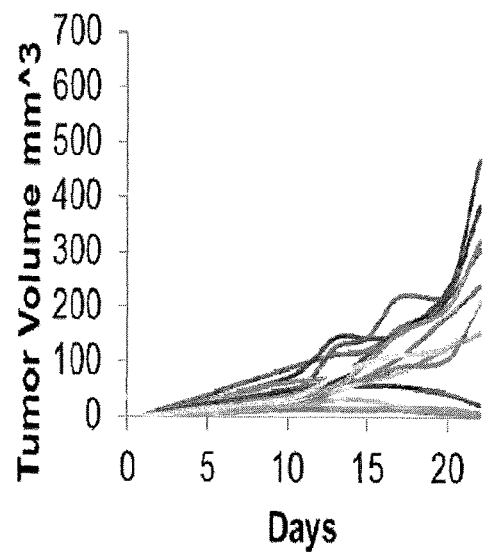
FIG. 9A-D. Individual tumor progression curves. Individual tumor progression curves for the mice treated with PBS (A), an anti-murine CEACAM1 antibody (B), an anti-murine PD-1 antibody (C) or a combination of both antibodies (D).
Figure 9B:
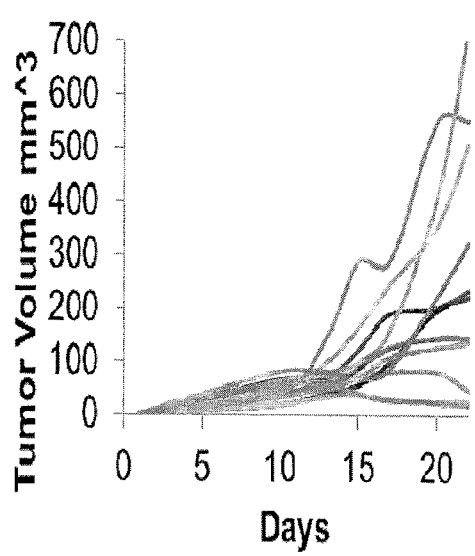
Figure 9C:
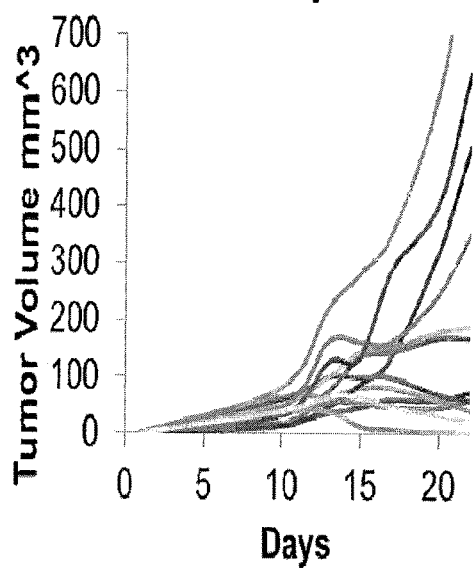
Figure 9D:
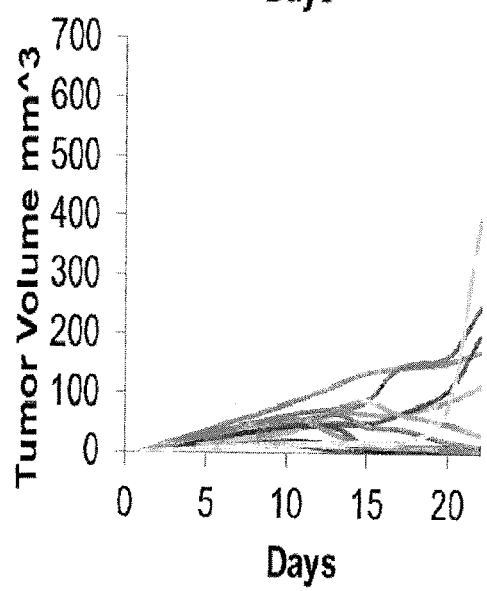

FIG. 8 demonstrates that anti-CEACAM1 antibodies and anti-PD-1/PD-L1/PD-L2 antibodies are able to bind their respective targets on tumor cells and/or immune cells in-vivo, and that this combined binding significantly attenuates tumor progression compared to each mono-therapy. This result is highly important, as it attests to the efficacy and potential of the use of a combined anti-CEACAM1 and anti-PD-1/PD-L1/PD-L2 even in established tumors of considerable volumes, which mimic the clinical setting where patients with established tumors are being treated FIG. 9 provides tumor progression curves for each individual mouse, grouped by their respective therapies (control, anti-CEACAM1 antibodies, anti-PD-1 antibodies, or a combination of anti-CEACAM1 and anti-PD-1 antibodies).

Example 9—Treatment of a Cancer Xenograft Model with a Combination of an Anti-CEACAM-1 Antibody and an Anti-PD-1 or Anti-PD-L1 Antibody Tumors are xenografted into SCID NOD mice by sub-cutaneous (SC) injection of a cancer cell line (e.g. melanoma cell line such as SKMELS). The effect of an anti-CEACAM-1 antibody (e.g. CM-24) alone, the effect of a monoclonal antibody to human PD-1 or a monoclonal antibody to human PD-L1 alone, and the effect of a combination of both antibodies, with or without TIL cells is examined by tumor eradication, tumor growth inhibition and/or mice mortality rate.

For example, SCID-NOD mice are randomized into the groups disclosed in Table 2.

TABLE 2

SCID-NOD mice groups.

| Group | Test item | No of animals |
|---|---|---|
| 1 | Control IgG | 10 |
| 2 | Anti-CEACAM-1 antibody | 10 |
| 3 | Anti PD-1 antibody | 10 |
| 4 | Anti-CEACAM-1 antibody + Anti PD-1 antibody | 10 |
| 5 | Control IgG + TIL* | 10 |
| 6 | Anti-CEACAM-1 antibody + TIL* | 10 |
| 7 | Anti PD-1 antibody + TIL* | 10 |
| 8 | Anti-CEACAM-1 antibody + Anti PD-1 antibody + TIL* | 10 |

*TIL is adoptively administered in order to compensate on the absence of the immune system in this mouse strain.

Tumor initiation—Each mouse is administered with a cancer cells (e.g. melanoma) in PBS by SC injection to the mice right flank. Treatment—Treatment starts at the tumor inoculation day. Tumors growth measurements—Measurements are done twice a week, using a caliper by a person blind to the experiment procedure. The measurements start from tumor initiation day. End point—~60-80 days from tumor initiation day. At assay termination day, all mice are sacrificed after total body bleeding and sera separation. Tumors are transferred to fixation in separate tube per mouse.

Example 10—Anti-PD-1/Anti-PD-L1//Anti-PD-L2/Anti-CEACAM1 Monotherapy Versus a Combination of Anti-CEACAM1 and Anti-PD-1/Anti-PD-L1/Anti-PD-L2 Therapy in Human Subjects with Untreated, Unresectable or Metastatic Cancer

| Group | Test item | No of subjects |
|---|---|---|
| 1 | A monoclonal antibody to human CEACAM1 solution administered intravenously every 2 weeks* | 10 |
| 2 | Anti PD-1 and/or anti PD-L1 and/or anti PD-L2 solution administered intravenously every 2 weeks* | 10 |
| 3 | A monoclonal antibody to human CEACAM1 solution administered intravenously, combined with anti PD-1 and/or anti PDL-1 and/or anti PD-L2 solution administered intravenously every 2 weeks, then a monoclonal antibody to human CEACAM1 solution administered intravenously every 3 weeks* | 10 |

*The Experiment continues until documented disease progression, discontinuation due to toxicity, withdrawal of consent of the subject or the end of the study.

The invention claimed is:

1. A composition comprising:
    a pharmaceutical composition comprising a monoclonal antibody to human CEACAM1 or an antigen-binding fragment thereof having a heavy-chain CDR1 comprising a sequence set forth in SEQ ID NO: 1, a heavy-chain CDR2 comprising a sequence set forth in SEQ ID NO: 2, a heavy-chain CDR3 comprising a sequence set forth in SEQ ID NO: 3, a light-chain CDR1 comprising a sequence set forth in SEQ ID NO: 4, a light-chain CDR2 comprising a sequence set forth in SEQ ID NO: 5 and a light-chain CDR3 comprising a sequence set forth in SEQ ID NO: 6; and
    a pharmaceutical composition comprising a monoclonal antibody to at least one of human PD-1, PD-L1 and PD-L2 or an antigen-binding fragment thereof, capable of disrupting the binding of PD-1 to its ligands;
wherein said pharmaceutical compositions are in separate containers.

2. The composition of claim 1, comprising a monoclonal antibody to human CEACAM1 and a monoclonal antibody to human PD-1.

3. The composition of claim 1, wherein said monoclonal antibody to human CEACAM1 or an antigen-binding fragment thereof is capable of binding with an affinity of at least about $10^{-8}$M to human CEACAM1.

4. The composition of claim 1, wherein said monoclonal antibody to human CEACAM1 or an antigen-binding fragment thereof is capable of binding with an affinity of at least about $5 \times 10^{-7}$M to at least one of human CEACAM3 and human CEACAM5.

5. The composition of claim 1, wherein said monoclonal antibody to human CEACAM1 is CM-24 or an antigen-binding fragment thereof.

6. The composition of claim 2, wherein said monoclonal antibody to human PD-1 is selected from the group consisting of MK-3475, AMP514, BMS-936558, CT-011, antigen-binding fragments thereof, and any combination thereof.

7. The composition of claim 1, wherein said monoclonal antibodies are human or humanized monoclonal antibodies.

8. The composition of claim 1, further comprising a human lymphocyte cell.

9. A method for treating a patient having cancer, comprising the steps of separately administering to said patient:
(i) a pharmaceutical composition comprising a monoclonal antibody to human CEACAM1 or an antigen-binding fragment thereof, capable of blocking CEACAM1 ligand having a heavy-chain CDR1 comprising a sequence set forth in SEQ ID NO: 1, a heavy-chain CDR2 comprising a sequence set forth in SEQ ID NO: 2, a heavy-chain CDR3 comprising a sequence set forth in SEQ ID NO: 3, a light-chain CDR1 comprising a sequence set forth in SEQ ID NO: 4, a light-chain CDR2 comprising a sequence set forth in SEQ ID NO: 5 and a light-chain CDR3 comprising a sequence set forth in SEQ ID NO: 6; and
(ii) a pharmaceutical composition comprising a monoclonal antibody to at least one of human PD-1, PD-L1 and PD-L2 or an antigen-binding fragment thereof, capable of disrupting the binding of PD-1 to its ligands; thereby treating said cancer.

10. The method of claim 9, comprising separately administering to said patient:
(i) a pharmaceutical composition comprising said monoclonal antibody to human CEACAM1 or an antigen-binding fragment thereof; and
(ii) a pharmaceutical composition comprising said monoclonal antibody to human PD-1 or an antigen-binding fragment thereof.

11. The method of claim 9, wherein said monoclonal antibody to human PD-1, PD-L1 and PD-L2 is administered to said patient before said monoclonal antibody to human CEACAM1.

12. The method of claim 9, wherein said monoclonal antibody to human PD-1, PD-L1 and PD-L2 is administered to said patient simultaneously with said monoclonal antibody to human CEACAM1.

13. The method of claim 9, wherein said monoclonal antibody to human PD-1, PD-L1 and PD-L2 is administered to said patient after said monoclonal antibody to human CEACAM1.

14. The method of claim 9, further comprising administering to said patient a pharmaceutical composition comprising a lymphocyte cell.

15. The method of claim 9, wherein said cancer expresses CEACAM1, PD-1, PD-L1, PD-L2, or any combination thereof.

16. The method of claim 9, wherein said cancer is selected from the group consisting of a melanoma, lymphoma, lung, thyroid, breast, colon, prostate, hepatic, bladder, renal, cervical, pancreatic, leukemia, myeloid, ovarian, uterus, sarcoma, biliary, and endometrial cells cancers.

17. A kit comprising:
(i) a pharmaceutical composition comprising a monoclonal antibody to human CEACAM1 or an antigen-binding fragment thereof, having a heavy-chain CDR1 comprising a sequence set forth in SEQ ID NO: 1, a heavy-chain CDR2 comprising a sequence set forth in SEQ ID NO: 2, a heavy-chain CDR3 comprising a sequence set forth in SEQ ID NO: 3, a light-chain CDR1 comprising a sequence set forth in SEQ ID NO: 4, a light-chain CDR2 comprising a sequence set forth in SEQ ID NO: 5 and a light-chain CDR3 comprising a sequence set forth in SEQ ID NO: 6; and
(ii) a pharmaceutical composition comprising a monoclonal antibody to at least one of human PD-1, PD-L1 and PD-L2 or an antigen-binding fragment thereof, capable of disrupting the binding of PD-1 to its ligands.

18. The composition of claim 1, wherein said monoclonal antibody to human PD-L1 is selected from the group consisting of MEDI-4736, BMS-936559, MSB0010718C, MPDL3280A, antigen-binding fragments thereof, and any combination thereof.

* * * * *

SEQUENCE LISTING

<160> NUMBER OF SEQ ID NOS: 31

<210> SEQ ID NO 1
<211> LENGTH: 5
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: X is Absent or Thr
<220> FEATURE:
<221> NAME/KEY: MISC_FEATURE
<222> LOCATION: (5)..(5)
<223> OTHER INFORMATION: X is Absent or Ile

<400> SEQUENCE: 1

Xaa Asn Asn Leu Xaa
1               5

<210> SEQ ID NO 2
<211> LENGTH: 8
<212> TYPE: PRT
<213> ORGANISM: Mus musculus

<400> SEQUENCE: 2

Ile Asn Pro Gly Ser Gly Asp Thr
1               5

<210> SEQ ID NO 3
<211> LENGTH: 11
<212> TYPE: PRT
<213> ORGANISM: Mus musculus

<400> SEQUENCE: 3

Gly Asp Tyr Tyr Gly Gly Phe Ala Val Asp Tyr
1               5                   10

<210> SEQ ID NO 4
<211> LENGTH: 6
<212> TYPE: PRT
<213> ORGANISM: Mus musculus

<400> SEQUENCE: 4

Gln Asp Ile Gly Asn Tyr
1               5

<210> SEQ ID NO 5
<211> LENGTH: 4
<212> TYPE: PRT
<213> ORGANISM: Mus musculus

<400> SEQUENCE: 5

Tyr Thr Ser Arg
1

<210> SEQ ID NO 6
<211> LENGTH: 7
<212> TYPE: PRT
<213> ORGANISM: Mus musculus

<400> SEQUENCE: 6

Gln Gln Gly Lys Ser Leu Pro
1               5

```
<210> SEQ ID NO 7
<211> LENGTH: 5
<212> TYPE: PRT
<213> ORGANISM: Mus musculus

<400> SEQUENCE: 7

Asn Asn Leu Ile Glu
1               5

<210> SEQ ID NO 8
<211> LENGTH: 17
<212> TYPE: PRT
<213> ORGANISM: Mus musculus

<400> SEQUENCE: 8

Val Ile Asn Pro Gly Ser Gly Asp Thr Asn Tyr Asn Glu Lys Phe Lys
1               5                   10                  15

Gly

<210> SEQ ID NO 9
<211> LENGTH: 11
<212> TYPE: PRT
<213> ORGANISM: Mus musculus

<400> SEQUENCE: 9

Gly Asp Tyr Tyr Gly Gly Phe Ala Val Asp Tyr
1               5                   10

<210> SEQ ID NO 10
<211> LENGTH: 11
<212> TYPE: PRT
<213> ORGANISM: Mus musculus

<400> SEQUENCE: 10

Arg Thr Ser Gln Asp Ile Gly Asn Tyr Leu Asn
1               5                   10

<210> SEQ ID NO 11
<211> LENGTH: 7
<212> TYPE: PRT
<213> ORGANISM: Mus musculus

<400> SEQUENCE: 11

Tyr Thr Ser Arg Leu His Ser
1               5

<210> SEQ ID NO 12
<211> LENGTH: 7
<212> TYPE: PRT
<213> ORGANISM: Mus musculus

<400> SEQUENCE: 12

Gln Gln Gly Lys Ser Leu Pro
1               5

<210> SEQ ID NO 13
<211> LENGTH: 8
<212> TYPE: PRT
<213> ORGANISM: Mus musculus

<400> SEQUENCE: 13

Gly Tyr Ala Phe Thr Asn Asn Leu
1               5
```

```
<210> SEQ ID NO 14
<211> LENGTH: 8
<212> TYPE: PRT
<213> ORGANISM: Mus musculus

<400> SEQUENCE: 14

Ile Asn Pro Gly Ser Gly Asp Thr
1               5

<210> SEQ ID NO 15
<211> LENGTH: 13
<212> TYPE: PRT
<213> ORGANISM: Mus musculus

<400> SEQUENCE: 15

Ala Arg Gly Asp Tyr Tyr Gly Gly Phe Ala Val Asp Tyr
1               5                   10

<210> SEQ ID NO 16
<211> LENGTH: 6
<212> TYPE: PRT
<213> ORGANISM: Mus musculus

<400> SEQUENCE: 16

Gln Asp Ile Gly Asn Tyr
1               5

<210> SEQ ID NO 17
<211> LENGTH: 4
<212> TYPE: PRT
<213> ORGANISM: Mus musculus

<400> SEQUENCE: 17

Tyr Thr Ser Arg
1

<210> SEQ ID NO 18
<211> LENGTH: 9
<212> TYPE: PRT
<213> ORGANISM: Mus musculus

<400> SEQUENCE: 18

Gln Gln Gly Lys Ser Leu Pro Arg Thr
1               5

<210> SEQ ID NO 19
<211> LENGTH: 10
<212> TYPE: PRT
<213> ORGANISM: Mus musculus

<400> SEQUENCE: 19

Gly Tyr Ala Phe Thr Asn Asn Leu Ile Glu
1               5                   10

<210> SEQ ID NO 20
<211> LENGTH: 17
<212> TYPE: PRT
<213> ORGANISM: Mus musculus

<400> SEQUENCE: 20

Val Ile Asn Pro Gly Ser Gly Asp Thr Asn Tyr Asn Glu Lys Phe Lys
1               5                   10                  15

Gly
```

<210> SEQ ID NO 21
<211> LENGTH: 13
<212> TYPE: PRT
<213> ORGANISM: Mus musculus

<400> SEQUENCE: 21

Ala Arg Gly Asp Tyr Tyr Gly Gly Phe Ala Val Asp Tyr
1               5                   10

<210> SEQ ID NO 22
<211> LENGTH: 11
<212> TYPE: PRT
<213> ORGANISM: Mus musculus

<400> SEQUENCE: 22

Arg Thr Ser Gln Asp Ile Gly Asn Tyr Leu Asn
1               5                   10

<210> SEQ ID NO 23
<211> LENGTH: 7
<212> TYPE: PRT
<213> ORGANISM: Mus musculus

<400> SEQUENCE: 23

Tyr Thr Ser Arg Leu His Ser
1               5

<210> SEQ ID NO 24
<211> LENGTH: 9
<212> TYPE: PRT
<213> ORGANISM: Mus musculus

<400> SEQUENCE: 24

Gln Gln Gly Lys Ser Leu Pro Arg Thr
1               5

<210> SEQ ID NO 25
<211> LENGTH: 120
<212> TYPE: PRT
<213> ORGANISM: artificial sequence
<220> FEATURE:
<223> OTHER INFORMATION: Recombinant polypeptide

<400> SEQUENCE: 25

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Asn
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Asp Thr Asn Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Asp Asp Ser Ala Val Tyr Phe Cys
                85                  90                  95

Ala Arg Gly Asp Tyr Tyr Gly Gly Phe Ala Val Asp Tyr Trp Gly Gln
            100                 105                 110

Gly Thr Ser Val Thr Val Ser Ser
        115                 120

```
<210> SEQ ID NO 26
<211> LENGTH: 107
<212> TYPE: PRT
<213> ORGANISM: artificial sequence
<220> FEATURE:
<223> OTHER INFORMATION: Recombinant polypeptide

<400> SEQUENCE: 26
```

Asp Ile Gln Met Thr Gln Thr Thr Ser Ser Leu Ser Ala Ser Leu Gly
1               5                   10                  15

Asp Arg Val Thr Ile Ser Cys Arg Thr Ser Gln Asp Ile Gly Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Lys Ser Leu Pro Arg
                85                  90                  95

Thr Phe Gly Gly Gly Thr Lys Leu Glu Ile Lys
            100                 105

```
<210> SEQ ID NO 27
<211> LENGTH: 450
<212> TYPE: PRT
<213> ORGANISM: artificial sequence
<220> FEATURE:
<223> OTHER INFORMATION: Recombinant polypeptide

<400> SEQUENCE: 27
```

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Asn
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Asp Thr Asn Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Asp Asp Ser Ala Val Tyr Phe Cys
                85                  90                  95

Ala Arg Gly Asp Tyr Tyr Gly Gly Phe Ala Val Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

```
Pro Ser Asn Thr Lys Val Asp Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 28
<211> LENGTH: 214
<212> TYPE: PRT
<213> ORGANISM: artificial sequence
<220> FEATURE:
<223> OTHER INFORMATION: Recombinant polypeptide

<400> SEQUENCE: 28

Asp Ile Gln Met Thr Gln Thr Thr Ser Ser Leu Ser Ala Ser Leu Gly
1               5                   10                  15

Asp Arg Val Thr Ile Ser Cys Arg Thr Ser Gln Asp Ile Gly Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Lys Ser Leu Pro Arg
                85                  90                  95

Thr Phe Gly Gly Gly Thr Lys Leu Glu Ile Lys Arg Thr Val Ala Ala
                100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 29
<211> LENGTH: 13
<212> TYPE: PRT
<213> ORGANISM: Homo sapiens

<400> SEQUENCE: 29

Val Leu Leu Leu Val His Asn Leu Pro Gln Gln Leu Phe
1               5                   10

<210> SEQ ID NO 30
<211> LENGTH: 12
<212> TYPE: PRT
<213> ORGANISM: Homo sapiens

<400> SEQUENCE: 30

Tyr Pro Asn Ala Ser Leu Leu Ile Gln Asn Val Thr
1               5                   10

<210> SEQ ID NO 31
<211> LENGTH: 7
<212> TYPE: PRT
<213> ORGANISM: Homo sapiens

<400> SEQUENCE: 31

Pro Asn Ala Ser Leu Leu Ile
1               5
```